(12) United States Patent
Wang et al.

(10) Patent No.: US 10,136,804 B2
(45) Date of Patent: Nov. 27, 2018

(54) AUTOMATIC FUNDUS IMAGE CAPTURE SYSTEM

(71) Applicant: Welch Allyn, Inc., Skaneateles Falls, NY (US)

(72) Inventors: Ynjiun Paul Wang, Cupertino, CA (US); Ervin Goldfain, Syracuse, NY (US); Raymond A. Lia, Auburn, NY (US); David J. Maier, Skaneateles, NY (US); Kenzi L. Mudge, Skaneateles, NY (US); Jon R. Salvati, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 164 days.

(21) Appl. No.: 15/009,988

(22) Filed: Jan. 29, 2016

(65) Prior Publication Data

US 2017/0020389 A1 Jan. 26, 2017

Related U.S. Application Data

(60) Provisional application No. 62/196,580, filed on Jul. 24, 2015.

(51) Int. Cl.
*A61B 3/14* (2006.01)
*A61B 3/00* (2006.01)
(Continued)

(52) U.S. Cl.
CPC .............. *A61B 3/0025* (2013.01); *A61B 3/12* (2013.01); *G06K 9/0061* (2013.01); *G06K 9/00604* (2013.01)

(58) Field of Classification Search
CPC ......... A61B 3/0025; A61B 3/102; A61B 3/12; A61B 3/0033; A61B 3/0058; A61B 3/024;
(Continued)

(56) References Cited

U.S. PATENT DOCUMENTS 5,599,276 A 2/1997 Hauptli et al.
5,703,621 A * 12/1997 Martin ................. G09G 3/2044
345/690

(Continued)

FOREIGN PATENT DOCUMENTS

CN 102324014 A 1/2012
CN 102626304 A 8/2012
(Continued)

OTHER PUBLICATIONS

International Search Report and Written Opinion for Application No. PCT/US2016/042940 dated Oct. 27, 2016, 14 pages.
(Continued)

*Primary Examiner* — Nathnael Aynalem
(74) *Attorney, Agent, or Firm* — Merchant & Gould P.C.

(57) ABSTRACT

A system automatically captures a fundus image with limited user interaction such that the fundus image has one or more desired characteristics. The system can retrieve at least one image from an image capture device, process the at least one image digitally to generate a processed image, detect at least one point of interest in the processed image, determine that each of the at least one point of interest is representative of a corresponding feature of the eye, and obtain a fundus image of the eye based on the at least one image.

16 Claims, 19 Drawing Sheets

(51) Int. Cl.
  *A61B 3/12* (2006.01)
  *G06K 9/00* (2006.01)

(58) Field of Classification Search
  CPC .......... A61B 3/14; A61B 3/0041; A61B 3/18;
              G06F 19/3406; G06T 2207/10101; G06T
              2207/30041; G06T 2207/30168; G06T
              5/50
  USPC ...................... 351/206, 246, 208
  See application file for complete search history.

(56) References Cited

U.S. PATENT DOCUMENTS

| | | |
|---|---|---|
| 5,784,148 A | 7/1998 | Heacock |
| 5,943,116 A | 8/1999 | Zeimer |
| 6,000,799 A | 12/1999 | Van de Velde |
| 6,120,461 A | 9/2000 | Smyth |
| 6,296,358 B1 | 10/2001 | Cornsweet et al. |
| 6,307,526 B1 | 10/2001 | Mann |
| 6,309,070 B1 | 10/2001 | Svetliza et al. |
| 6,325,511 B1 | 12/2001 | Mizouchi |
| 6,350,031 B1 | 2/2002 | Lashkari et al. |
| 6,556,853 B1 | 4/2003 | Cabib et al. |
| 7,264,355 B2 | 9/2007 | Rathjen |
| 7,284,859 B2 | 10/2007 | Ferguson |
| 7,311,400 B2 | 12/2007 | Wakil et al. |
| 7,364,297 B2 | 4/2008 | Goldfain et al. |
| 7,380,938 B2 | 6/2008 | Chmielewski, Jr. et al. |
| 7,387,384 B2 | 6/2008 | Heine et al. |
| 7,404,640 B2 | 7/2008 | Ferguson et al. |
| 7,470,024 B2 | 12/2008 | Chinaglia et al. |
| 7,488,294 B2 | 2/2009 | Torch |
| 7,568,628 B2 | 8/2009 | Wang et al. |
| 7,611,060 B2 | 11/2009 | Wang et al. |
| 7,621,636 B2 | 11/2009 | Su et al. |
| 7,784,940 B2 | 8/2010 | Goldfain et al. |
| 7,809,160 B2 | 10/2010 | Vertegaal et al. |
| 7,871,164 B2 | 1/2011 | Luther et al. |
| 7,926,945 B2 | 4/2011 | Dick et al. |
| 7,963,653 B1 | 6/2011 | Ellman |
| 7,976,162 B2 | 7/2011 | Flitcroft |
| 8,109,634 B2 | 2/2012 | Gil |
| 8,347,106 B2 | 1/2013 | Tsuria et al. |
| 8,366,270 B2 | 2/2013 | Pujol Ramo et al. |
| 8,388,523 B2 | 3/2013 | Vivenzio et al. |
| 8,444,269 B1 | 5/2013 | Ellman |
| 8,488,895 B2 | 7/2013 | Muller et al. |
| 8,534,837 B2 | 9/2013 | Sayeram et al. |
| 8,577,644 B1* | 11/2013 | Ksondzyk ............. G06F 3/0414 345/173 |
| 8,585,203 B2 | 11/2013 | Aikawa et al. |
| 8,620,048 B2 | 12/2013 | Nakano et al. |
| 8,649,008 B2 | 2/2014 | Kashani et al. |
| 8,696,122 B2 | 4/2014 | Hammer et al. |
| 8,714,743 B2 | 5/2014 | Verdooner |
| 8,879,813 B1 | 11/2014 | Solanki et al. |
| 9,211,064 B2 | 12/2015 | Wang |
| 9,237,847 B2 | 1/2016 | Wang et al. |
| 9,498,126 B2 | 11/2016 | Wang |
| 9,757,031 B2 | 9/2017 | Wang et al. |
| 9,918,629 B2 | 3/2018 | Wang |
| 2002/0101568 A1 | 8/2002 | Eberl et al. |
| 2003/0071970 A1 | 4/2003 | Donnerhacke et al. |
| 2003/0208125 A1 | 11/2003 | Watkins |
| 2005/0012899 A1 | 1/2005 | Ferguson |
| 2005/0043588 A1 | 2/2005 | Tsai |
| 2005/0110949 A1 | 5/2005 | Goldfain et al. |
| 2005/0254008 A1 | 11/2005 | Ferguson et al. |
| 2006/0113386 A1 | 6/2006 | Olmstead |
| 2006/0119858 A1 | 6/2006 | Knighton et al. |
| 2006/0147095 A1 | 7/2006 | Usher et al. |
| 2006/0202036 A1 | 9/2006 | Wang et al. |
| 2006/0202038 A1 | 9/2006 | Wang et al. |
| 2006/0268231 A1 | 11/2006 | Gil et al. |
| 2007/0174152 A1 | 7/2007 | Bjornberg et al. |
| 2007/0188706 A1 | 8/2007 | Pearson et al. |
| 2008/0084538 A1 | 4/2008 | Maeda et al. |
| 2008/0231803 A1 | 9/2008 | Feldon et al. |
| 2008/0316426 A1 | 12/2008 | Shibata et al. |
| 2009/0096885 A1* | 4/2009 | Robinson ............. H04N 5/23212 348/222.1 |
| 2009/0225277 A1 | 9/2009 | Gil |
| 2009/0275929 A1 | 11/2009 | Zickler |
| 2009/0316115 A1 | 12/2009 | Itch et al. |
| 2010/0014052 A1 | 1/2010 | Koschmieder et al. |
| 2010/0085538 A1 | 4/2010 | Masaki et al. |
| 2010/0110375 A1* | 5/2010 | Nishio ................. A61B 3/102 351/206 |
| 2010/0149489 A1 | 6/2010 | Kikawa et al. |
| 2010/0208961 A1 | 8/2010 | Zahniser |
| 2010/0238402 A1 | 9/2010 | Itoh et al. |
| 2011/0001927 A1 | 1/2011 | Kasper |
| 2011/0028513 A1 | 2/2011 | Zhuo et al. |
| 2011/0043756 A1 | 2/2011 | Kahn et al. |
| 2011/0169935 A1 | 7/2011 | Henriksen |
| 2011/0234977 A1 | 9/2011 | Verdooner |
| 2011/0242306 A1 | 10/2011 | Bressler et al. |
| 2011/0299034 A1* | 12/2011 | Walsh .................. A61B 3/102 351/206 |
| 2011/0299036 A1 | 12/2011 | Goldenholz |
| 2012/0050677 A1 | 3/2012 | Ohban |
| 2012/0121158 A1 | 5/2012 | Sekine et al. |
| 2012/0147327 A1 | 6/2012 | Shikaumi et al. |
| 2012/0169995 A1 | 7/2012 | Mohr et al. |
| 2012/0200690 A1 | 8/2012 | Beasley |
| 2012/0213423 A1 | 8/2012 | Xu et al. |
| 2012/0218301 A1 | 8/2012 | Miller |
| 2012/0229617 A1 | 9/2012 | Yates et al. |
| 2012/0229764 A1 | 9/2012 | Tomatsu et al. |
| 2012/0248196 A1 | 10/2012 | Wang |
| 2012/0249956 A1 | 10/2012 | Narasimha-Iyer et al. |
| 2012/0257163 A1 | 10/2012 | Dyer et al. |
| 2012/0320340 A1 | 12/2012 | Coleman, III |
| 2013/0010260 A1 | 1/2013 | Tumlinson et al. |
| 2013/0016320 A1 | 1/2013 | Naba |
| 2013/0057828 A1 | 3/2013 | de Smet |
| 2013/0063698 A1 | 3/2013 | Akiba et al. |
| 2013/0169934 A1 | 7/2013 | Verdooner |
| 2013/0176533 A1 | 7/2013 | Raffle et al. |
| 2013/0194548 A1 | 8/2013 | Francis et al. |
| 2013/0201449 A1 | 8/2013 | Walsh et al. |
| 2013/0208241 A1 | 8/2013 | Lawson et al. |
| 2013/0211285 A1 | 8/2013 | Fuller et al. |
| 2013/0215387 A1 | 8/2013 | Makihira et al. |
| 2013/0222763 A1 | 8/2013 | Bublitz et al. |
| 2013/0229622 A1 | 9/2013 | Murase et al. |
| 2013/0234930 A1 | 9/2013 | Palacios Goerger |
| 2013/0250237 A1 | 9/2013 | Ueno |
| 2013/0250242 A1 | 9/2013 | Cheng et al. |
| 2014/0022270 A1 | 1/2014 | Rice-Jones et al. |
| 2014/0104573 A1 | 4/2014 | Iwanaga |
| 2014/0192320 A1 | 7/2014 | Tsao |
| 2014/0198298 A1 | 7/2014 | Cheng et al. |
| 2014/0204340 A1 | 7/2014 | Verdooner |
| 2014/0211162 A1 | 7/2014 | Matsuoka et al. |
| 2014/0268046 A1* | 9/2014 | Narasimha-Iyer ..... A61B 3/102 351/206 |
| 2015/0002811 A1 | 1/2015 | Ota |
| 2015/0110348 A1 | 4/2015 | Solanki et al. |
| 2015/0150449 A1 | 6/2015 | Matsumoto |
| 2015/0170360 A1 | 6/2015 | Fletcher et al. |
| 2015/0178946 A1* | 6/2015 | Krishnaswamy ........ G06K 9/46 345/582 |
| 2016/0058284 A1 | 3/2016 | Wang |
| 2016/0081548 A1 | 3/2016 | Wang et al. |
| 2016/0092721 A1 | 3/2016 | Kanagasingam et al. |
| 2016/0166141 A1 | 6/2016 | Kanagasingam et al. |
| 2016/0213249 A1 | 7/2016 | Cornsweet et al. |
| 2016/0249804 A1 | 9/2016 | Wang |
| 2016/0307341 A1 | 10/2016 | Sato et al. |
| 2017/0035292 A1 | 2/2017 | Wang |
| 2017/0119241 A1 | 5/2017 | Farchione et al. |
| 2017/0161892 A1 | 6/2017 | Tellatin et al. |
| 2017/0181625 A1 | 6/2017 | Kawakami et al. |

(56) References Cited

U.S. PATENT DOCUMENTS

| | | | |
|---|---|---|---|
| 2017/0196452 | A1 | 7/2017 | Wang |
| 2017/0311800 | A1 | 11/2017 | Wang |
| 2017/0316565 | A1 | 11/2017 | Leahy et al. |
| 2017/0332903 | A1 | 11/2017 | Wang et al. |

FOREIGN PATENT DOCUMENTS

| | | |
|---|---|---|
| CN | 102917634 A | 2/2013 |
| CN | 205006859 U | 2/2016 |
| CN | 105433899 A | 3/2016 |
| CN | 205181314 U | 4/2016 |
| EP | 2 425 763 A1 | 7/2012 |
| GB | 2378600 A | 12/2003 |
| JP | 2006-101943 A | 4/2006 |
| JP | 2009-172157 A | 8/2009 |
| JP | 2009-219644 A | 10/2009 |
| JP | 2010-57547 A | 3/2010 |
| JP | 2011-097992 A | 5/2011 |
| JP | 2012-213575 A | 11/2012 |
| JP | 2013-46850 A | 3/2013 |
| JP | 2013-59551 | 4/2013 |
| JP | 2013-59551 A | 4/2013 |
| KR | 10-2013-001079 | 1/2013 |
| KR | 10-2013-0010079 A | 1/2013 |
| WO | 2004/089214 A2 | 10/2004 |
| WO | 2006/016366 A2 | 2/2006 |
| WO | 2008/106802 A1 | 9/2008 |
| WO | 2010/080576 A1 | 7/2010 |
| WO | 2010/115195 A1 | 10/2010 |
| WO | 2011/029064 A1 | 3/2011 |
| WO | 2012/009702 A1 | 1/2012 |
| WO | 2012/134272 A1 | 10/2012 |
| WO | 2013/041658 A1 | 3/2013 |
| WO | 2013/107464 A1 | 7/2013 |
| WO | 2014/182769 A1 | 11/2014 |
| WO | 2015/044366 A1 | 4/2015 |
| WO | 2015/170947 A1 | 11/2015 |

OTHER PUBLICATIONS

Anastasakis et al., SLO-Infrared Imaging of the Macula and its Correlation with Functional Loss and Structural Changes in Patients with Stargardt Disease, May 1, 2012, 19pgs.

Carrasco-Zevallos, O. et al., "Pupil Tracking Optical Coherence Tomography for Precise Control of Pupil Entry Position," Biomedical Optics Express: 6(9): 3405-3419, Sep. 1, 2015, 15pgs.

EIDON—The First True Color Confocal Scanner on the Market, www.centervue.com, Jul. 27, 2015, 12pgs.

Grieve et al., Multi-wavelength imaging with the adaptive optics scnaning laser Ophthalmoscope, Optics Express 12230, Dec. 11, 2006, vol. 14, No. 25, 13pgs.

Hammer et al., Adaptive Optics Scanning Laser Ophthalmoscope for Stablized Retinal Imaging, Optics Express: 14(8): 3354-3367, Apr. 17, 2006, 14pgs.

Markow et al., "Real-Time Algorithm for Retinal Tracking," IEEE Transactions on Biomedical Engineering; 40(12): 1269-1281, Dec. 1993, 13pgs.

Moscaritolo et al., "A Machine Vision Method for Automated Alignment of Fundus Imaging Systems," Ophthalmic Surgery Lasers & Imaging: 41(6): 607-613, Sep. 29, 2010, 7pgs.

Navilas, Navigated Laser Therapy—A New Era in Retinal Disease Management, www.od-os.com, © 2015, 16pgs.

Sahin et al., "Adaptive Optics with Pupil Tracking for High Resolution Retinal Imaging," Biomedical Optics Express: 3(2): 225-239, Feb. 1, 2012, 15pgs.

Sheehy et al., "High-speed, Image-based eye tracking with a scanning laser ophthalmoscope," Biomedical Optics Express; 3(10): 2611-2622, Oct. 1, 2012, 12pgs.

"A Portable, Scalable Retinal Imaging System," TI Engibous Competition Report (Spring 2012), Rice University, http://www.ti.com/corp/docs/university/docs/Rice_University_mobileVision%20Final%20Report.pdf (96 pages).

Brown et al., "Comparison of image-assisted versus traditional fundus examination," Eye and Brain, Dovepress, Feb. 2013, vol. 5, pp. 1-8.

Dilating Eye Drops, AAPOS, http://web.archive.org/web/2012020409024/http://www.aapos.org/terms/conditions/43, Dilating Eye Drops, 2pgs, Dec. 17, 2015.

Girdwain, "Goggles Differentiate Between Stroke and Vertigo," Today's Geriatric Medicine, vol. 6 No. 4 p. 8, 2 pages. (Oct. 1, 2013).

International Search Report and Written Opinion for Application No. PCT/US2015/013542 dated May 11, 2015, 12 pages.

International Search Report and Written Opinion for Application No. PCT/US2015/015124 dated May 15, 2015, 10 pages.

International International Search Report and Written Opinion for Application No. PCT/US2016/015653 dated May 3, 2016, 11 pages.

Johns Hopkins Medicine, "Small Johns Hopkins-led study finds portable device diagnoses stroke with 100 percent accuracy," www.hopkinsmedicine.org/se/util/display_mod.cfm?MODULE=/se-server/mod/modules/semod_printpage/mod_default.cfm&PageURL-/news/media/releases/is_i . . . , 2 pages (Mar. 5, 2013).

Muller et al., "Non-Mydriatic Confocal Retinal Imaging Using a Digital Light Projector," Ophthalmic Technologies XXIII, 2013, downloaded from: http://proceedings.spiedigitallibrary.org (8 pages).

Paques et al., "Panretinal, High-Resolution Color Photography of the Mouse Fundus," Investigative Ophthalmology & Visual Science, Jun. 2007, vol. 48, No. 6, pp. 2769-2774.

Spector,The Pupils, Clinical Methods: The History, Physical, and Laboratory Examinations, 3rd Edition, pp. 300-304, Chapter 58 (1990).

U.S. Appl. No. 15/009,988, filed Jan. 29, 2016 entitled "Automatic Fundus Image Capture System".

U.S. Appl. No. 15/054,558, filed Feb. 26, 2016 entitled "Retinal Image Capturing".

Visucampro NM—The Non-Mydriatic Fundus Camera System from Carl Zeiss, Carl Zeiss Meditec, International, 2005 (1 page).

Mayer et al., "Wavelet denoising of multiframe optical coherence tomography data," Biomedical Optics Express, vol. 3, No. 3, pp. 572-589 (Mar. 1, 2012).

\* cited by examiner

AUTOMATIC FUNDUS IMAGE CAPTURE SYSTEM

BACKGROUND

An ophthalmoscope is device used to image the fundus of an eye (or eye fundus) and other structures of the eye. The eye fundus image shows the interior surface of the eye opposite the lens, including the retina, optic disc, macula and fovea, and posterior pole. This imaging is used to determine the health of the retina and vitreous humor and to evaluate conditions such as hypertension, diabetic retinopathy, and papilledema. The ophthalmoscope device may include a camera that is used to capture the images and a display used to display the images obtained by the ophthalmoscope device. Medical professionals use the images to diagnose and treat various diseases.

Typically, the ophthalmoscope is a hand-held device or a headband-mounted device that is worn by a user, such as a caregiver or medical professional. To properly capture fundus images, the eye must be first aligned properly with the device. The user then interacts with the device to trigger a capture of an image. For example, the user needs to press a button or select a control on a graphic user interface (GUI) on the device to capture the image. However, a delay typically occurs between a time when the user decides to capture a fundus image and presses the button on the device and a time when the image is actually captured by the device. Further, the physical interaction with the device can cause unwanted movement of the device against the eye, thereby mislocating the eye fundus and producing a fundus image of inferior quality.

SUMMARY

In general terms, this disclosure is directed to an automatic fundus image capture system. In one possible configuration and by non-limiting example, the system is configured to automatically capture a fundus image with limited user interaction such that the fundus image has one or more desired characteristics. Various aspects are described in this disclosure, which include, but are not limited to, the following aspects.

One aspect is a method of automatically capturing a fundus image of an eye. The method includes retrieving at least one first image from an image sensor device; processing, using at least one computing device, the at least one first image digitally to generate a processed image; detecting at least one point of interest in the processed image; determining that each of the at least one point of interest is representative of a corresponding feature of the eye; and obtaining a fundus image of the eye based on the at least one first image.

Another aspect is an image capture device including: a processing device configured to control the image capture device; and a computer readable data storage device storing software instructions that, when executed by the processing device, cause the image capture device to: retrieve at least one first image from an image sensor device; process the at least one first image digitally to generate a processed image; detect at least one point of interest in the processed image; determine that each of the at least one point of interest is representative of a corresponding feature of the eye; and obtain a fundus image of the eye based on the at least one first image.

Yet another aspect is a system of automatically capturing a fundus image of an object. The system includes an image capture device configured to capture an image of an object, an image process device, and a display device configured to display the fundus image. The image process device is programmed to: retrieve a plurality of first images from the image capture device; process the plurality of first images digitally to generate a plurality of processed images; detect a point of interest in each of the processed images; determine that locations of the points of interests are substantially the same among the processed images; determine if one of the first images has a predetermined characteristic; if one of the first images has the predetermined characteristic, save that image as the fundus image; and if none of the first images has the predetermined characteristic, prompt the image capture device to capture a second image and save the second image as the fundus image, the second image having the predetermined characteristic.

DETAILED DESCRIPTION

Figure 1:
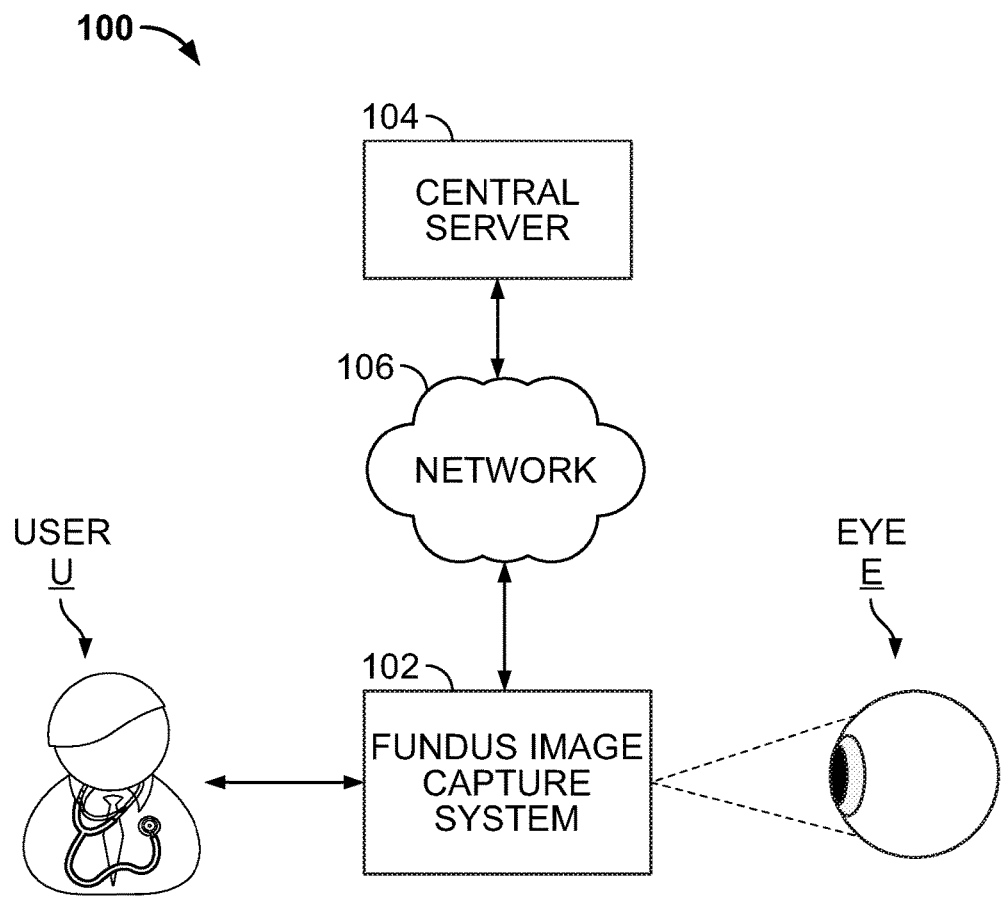
FIG. 1 is a schematic diagram illustrating an example system for automatically capturing a fundus image of an eye.

Various embodiments will be described in detail with reference to the drawings, wherein like reference numerals represent like parts and assemblies throughout the several views.

FIG. 1 is a schematic diagram illustrating an example system 100 for automatically capturing a fundus image of an eye E. In this example, the system 100 includes a fundus image capture system 102, a central server 104, and a network 106.

The fundus image capture system 102 is used to assist the user U in screening for, monitoring, and/or diagnosing various eye diseases or other diseases. As described herein, the fundus image capture system 102 is configured to capture one or more fundus images of the eye E of a subject (e.g., a patient). As used herein, "fundus" refers to the eye fundus and includes the retina, optic disc, macula and fovea, posterior pole, and other elements. The fundus image is reviewed by a user U, such as a caregiver and medical professional, for various purposes. For example, the fundus image can be used to screen the subject for eye diseases, or to diagnose or monitor the progression of various diseases. It will be appreciated that the user that operates the fundus image capture system 102 can be different from the user U evaluating the resulting fundus image.

As described herein, the fundus image capture system 102 is configured to automatically capture and process images without receiving a user interaction (e.g., a triggering action with a button or control on a graphic user interface of the system). In these examples, the fundus image capture system 102 can obtain a fundus image of desired quality without undue delay and/or unwanted movement due to the user interaction.

In some examples, at least a portion of the fundus image capture system 102 is configured to be held by the hand of the user U. In other examples, the fundus image capture system 102 is configured to be worn by the subject to capture the fundus image of the subject. Examples configurations of the fundus image capture system 102 are described in more detail with reference to FIG. 2.

In some embodiments, the system 100 can include the central server 104 that is in data communication with the fundus image capture system 102 via the network 106. The central server 104 is configured to receive data from the fundus image capture system 102 and perform additional processing and/or storage in an electronic medical record (EMR). In some examples, the fundus image capture system 102 is configured to send data associated with the images captured and/or processed therein to the central server 104, which then processes and store the data for various purposes.

The fundus image capture system 102 and the central server 104 communicate through the network 106. In one example, the fundus image capture system 102 and network 106 are part of a CONNEX™ system from Welch Allyn of Skaneateles Falls, N.Y., although other systems can be used. In such an example, the monitor devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

In another example, the central server 104 can be a distributed network, commonly referred to as a "cloud" server. The fundus image capture system 102 communicates with the cloud server through non-proprietary, industry standard messaging. Data encryption is also based on industry standards.

The network 106 is an electronic communication network that facilitates communication between the fundus image capture system 102 and the central server 104. An electronic communication network is a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Additionally, the network 106 includes networks formed between the fundus image capture system 102 and a peripheral device using a wireless network protocol (e.g., a mouse connected using Bluetooth, etc.).

Figure 2:
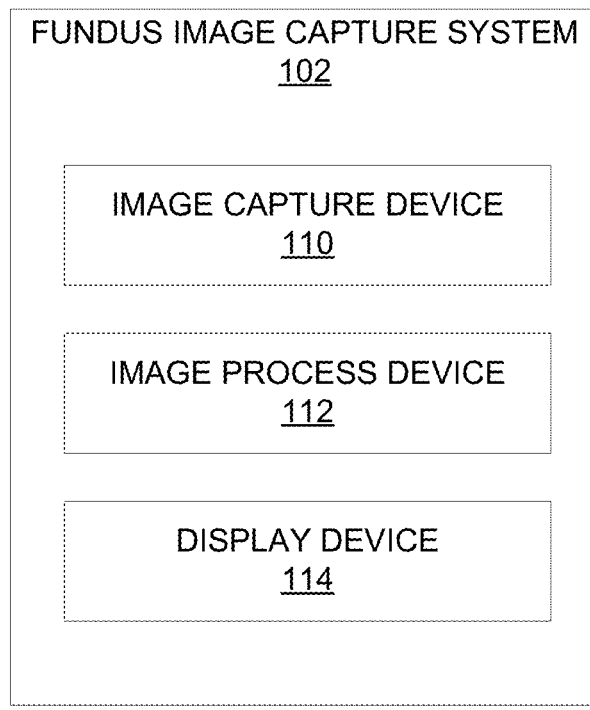
FIG. 2 illustrates an example of a fundus image capture system.

FIG. 2 illustrates an example of the fundus image capture system 102. In this example, the fundus image capture system 102 includes an image capture device 110, an image process device 112, and a display device 114.

The fundus image capture system 102 includes a physical structure configured to house and hold various components of the fundus image capture system 102. Such a physical structure can incorporate at least one of the image capture device 110, the image process device 112, and the display device 114.

In some embodiments, the physical structure of the fundus image capture system 102 is configured to be held by the user U for viewing and capturing images of the fundus. For example, the fundus image capture system 102 can be used with PanOptic™ Ophthalmoscope or iExaminer™ from Welch Allyn of Skaneateles Falls, N.Y. Other examples of the fundus image capture system 102 can employ at least part of the disclosure in U.S. patent application Ser. No. 14/633,601, titled THROUGH FOCUS RETINAL IMAGE CAPTURING, filed Feb. 27, 2015, the disclosure of which is incorporated herein by reference in its entirety. Another example fundus image capture system 102 is configured similarly to a device disclosed in U.S. patent application Ser. No. 14/557,146, titled DIGITAL COLPOSCOPE SYSTEM, filed Dec. 1, 2014, the entirety of which is incorporated herein by reference.

In other embodiments, the physical structure of the fundus image capture system 102 includes a support structure configured to couple to the subject (e.g., a patient). For example, the support structure is an eye glasses frame or a headband. An example of the physical structure of this type is disclosed in U.S. patent application Ser. No. 14/177,594, titled OPHTHALMOSCOPE DEVICE, filed Feb. 11, 2014, the disclosure of which is incorporated herein by reference in its entirety.

Yet other embodiments of the physical structure are also possible. In some examples, the physical structure of the fundus image capture system 102 includes all mechanical and electrical structures, and hardware and software as a single unit. In other examples, the fundus image capture system 102 is a digital ophthalmoscope that wirelessly transfers images to a computing device (e.g., mobile computing device or server) for processing. Other various examples are also possible.

The image capture device 110 is a device configured to capture images of the subject, such as the eye E of the subject. An example of the image capture device 110 is illustrated and described in more detail with reference to FIG. 3.

The image process device 112 is a device configured to retrieve one or more images from the image capture device 110 and process the images to obtain a fundus image as desired. As described herein, the image process device 112 operates to perform image processing to determine that a fundus image that has been captured suffices and/or to trigger the image capture device 110 to capture a desired fundus image. An example of the image process device 112 is illustrated and described in more detail with reference to FIG. 4.

The display device 114 is a device configured to display one or more images (e.g., one or more fundus images) in original and/or processed formats so that the user U reviews the images for diagnosis or monitoring. In some examples, the display device 114 is a display of a computing device, such as the screen of a mobile computing device (e.g., smartphones, tablets computers, and other mobile devices). In some embodiments, the image capture device 110, the image process device 112, and the display device 114 are implemented in a single computing device. In other embodiments, at least one of the image capture device 110, the image process device 112, and the display device 114 is implemented in different computing devices.

Figure 3:
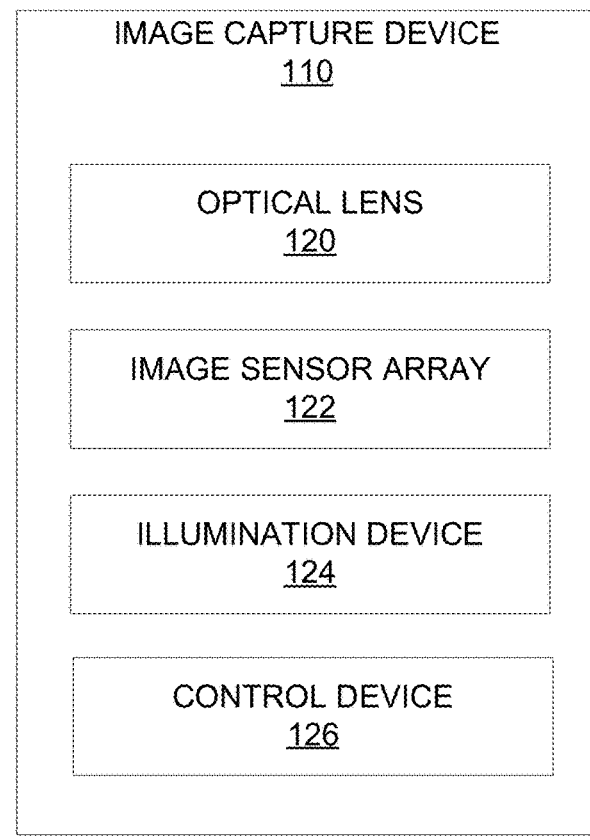
FIG. 3 illustrates an example of an image capture device of the fundus image capture system of FIG. 2.

FIG. 3 illustrates an example of the image capture device 110. In this example, the image capture device 110 includes an optical lens element 120, an image sensor array 122, an illumination device 124, and a control device 126.

The image capture device 110 is configured to capture images of the fundus of the subject. The image capture device 110 is in communication with the image process device 112. The images obtained by the image capture device 110 can be transmitted to the image process device 112 for subsequent processes. As described below, the image process device 112 can trigger the image capture device 110 to rapidly capture one or more images when the image process device 112 determines that the image capture device 110 is properly arranged to capture a fundus image as desired.

In some embodiments, the images captured by the image capture device 110 are digital images. The digital images can be captured in various formats, such as JPEG, BITMAP, TIFF, etc. In other embodiments, the images captured by the image capture device 110 are film images. In yet other embodiments, the image capture device 110 includes a digital video camera. Yet other embodiments of the image capture device 110 are possible as well.

In some examples, the optical lens element 120 includes a variable focal lens, such as a lens moved by a step motor, or a fluid lens (also known as a liquid lens). Other embodiments of the optical lens element 120 are also possible.

The image sensor array 122 is a device configured to receive and process light reflected by the subject's fundus. The image sensor array 122 can be of various types. For example, the image sensor array 122 is a complementary metal-oxide semiconductor (CMOS) sensor array (also known as an active pixel sensor (APS)) or a charge coupled device (CCD) sensor.

The example image sensor array 122 includes photodiodes that have a light-receiving surface and have substantially uniform length and width. During exposure, the photodiodes convert the incident light to a charge. The image sensor array 122 can be operated in various manners. In some embodiments, the image sensor array 122 is operated as a global reset, that is, substantially all of the photodiodes are exposed simultaneously and for substantially identical lengths of time. In other embodiments, the image sensor array 122 is used with a rolling shutter mechanism, in which exposures move as a wave from one side of an image to the other. Other mechanisms are also possible to operate the image sensor array 122 in yet other embodiments.

The illumination device 124 is a device configured to generate and direct light towards the eye of the subject when the image capture device 110 is in use so that the structures of the eye may be imaged. In some embodiments, the illumination device 124 includes one or more light emitting diodes, incandescent bulbs, or fiber optic cables. Yet other embodiments of the illumination device 124 are possible as well. In some embodiments, the illumination device 124 is configured to create multiple illumination conditions, each having a different intensity (i.e., brightness) of light. However, some embodiments of the image capture device 110 do not include an illumination device 124.

The control device 126 is a device configured to control the operation of the image capture device 110 to capture images. In some embodiments, the control device 126 is configured to control the optical lens element 120, the image sensor array 122, and the illumination device 124. In some embodiments, the control device 126 is in communication with the image process device 112.

Figure 4:
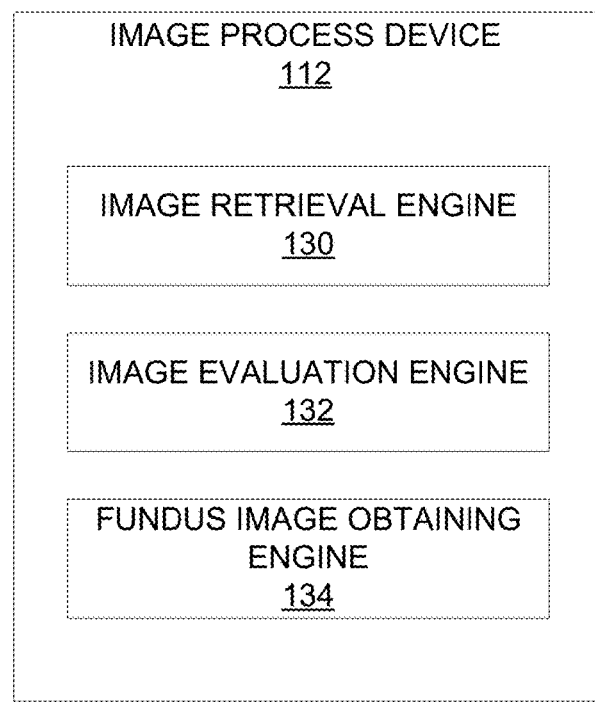
FIG. 4 illustrates an example of an image process device of the fundus image capture system of FIG. 2.

FIG. 4 illustrates an example of the image process device 112. In this example, the image process device 112 includes an image retrieval engine 130, an image evaluation engine 132, and a fundus image obtaining engine 134.

Figure 16:
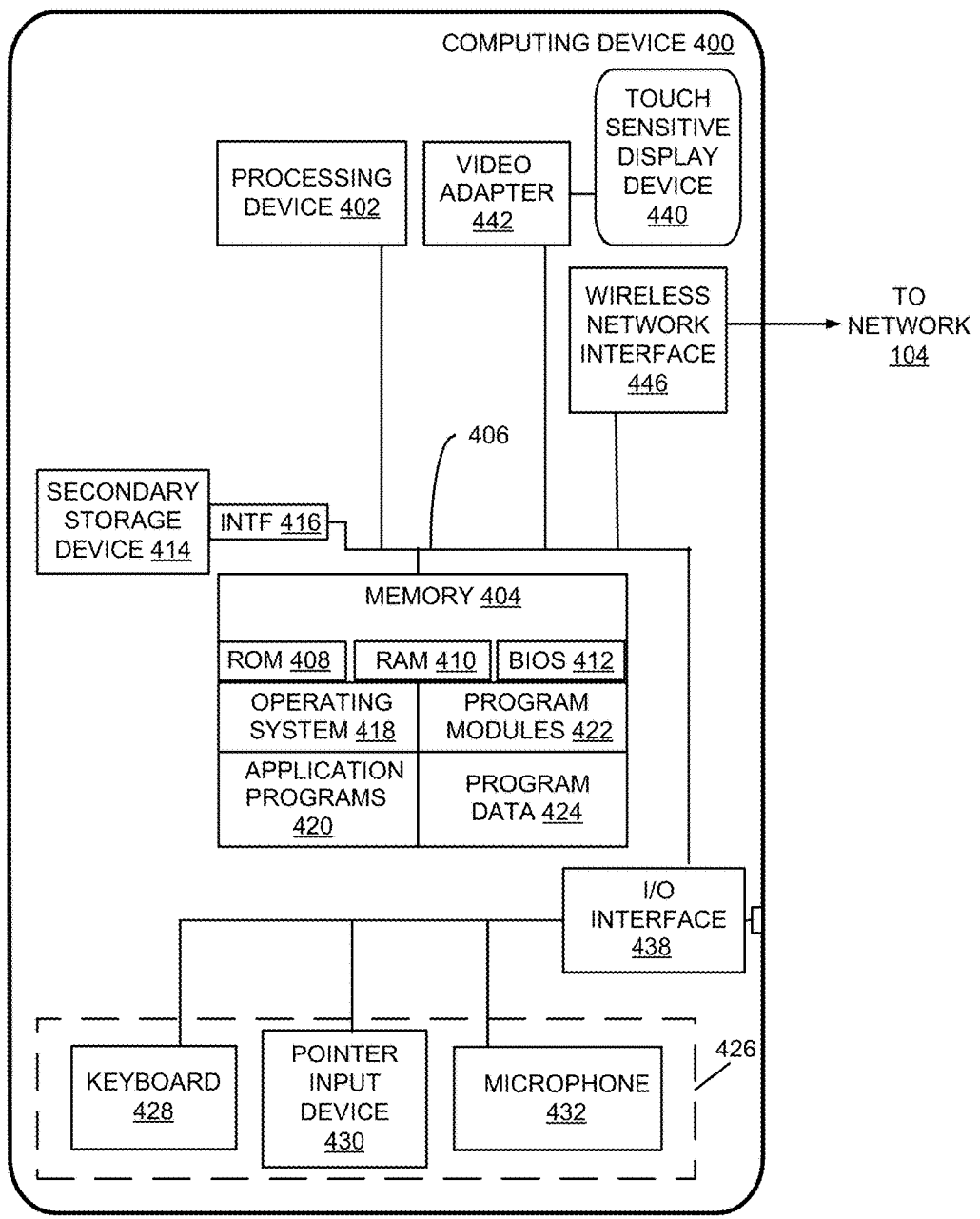
FIG. 16 illustrates an exemplary architecture of a computing device that can be used to implement aspects of the present disclosure.

In one implementation, the image retrieval engine 130, the image evaluation engine 132, and the fundus image obtaining engine 134 are implemented as a software application running on a computing device, as illustrated in FIG. 16. In some embodiments, the engines of the image process device 112 are developed with OpenCV library. Other libraries can also be used to implement the engines of the image process device 112.

The image retrieval engine 130 operates to interact with the image capture device 110 to retrieve images from the image capture device 110. In some examples, the image retrieval engine 130 interfaces with the image sensor array 122, either directly or through the control device 126, to obtain images collected in the image sensor array 122 in real-time.

The image evaluation engine 132 operates to determine whether a suitable fundus image has been captured by the image capture device 110. The image evaluation engine 132 operates to process the images retrieved by the image retrieval engine 130 to determine whether at least one of the images are acceptable as a fundus image. In some embodiments, the images are determined to be acceptable when they have one or more predetermined image characteristics. Examples of the image characteristics include an image quality and a size of the image.

The fundus image obtaining engine 134 operates to save the fundus image. In some embodiments, the fundus image obtaining engine 134 can trigger capturing an image of acceptable characteristic. For example, the fundus image obtaining engine 134 saves one or more of the images that have been retrieved from the image capture device 110 by the image retrieval engine 130, if the images have been determined by the image evaluation engine 132 to be acceptable as a fundus image. If the images are determined to be unacceptable, the fundus image obtaining engine 134 can simply return FALSE value. In this case, some embodiments of the image process device 112 returns to retrieve images (e.g., the operation 202 in FIG. 5). In other embodiments, if the images are determined to be unacceptable, the fundus image obtaining engine 134 can operate to trigger the image capture device 110 to rapidly capture one or more images that meet one or more predetermined image characteristics (e.g., a size and quality of image).

Figure 5:
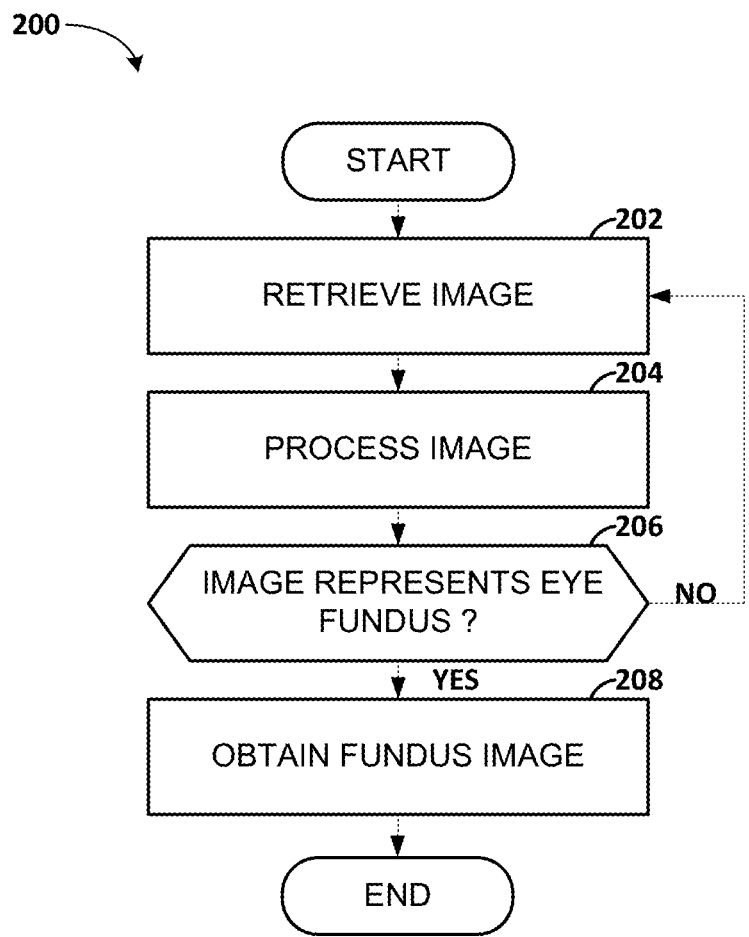
FIG. 5 is a flowchart illustrating an example operation of the image process device of FIG. 4.

FIG. 5 is a flowchart illustrating an example operation 200 of the image process device 112.

At operation 202, the image process device 112 retrieves one or more images collected by the image capture device 110. In some embodiments, the image process device 112 obtains the images in real-time. The operation 202 can be performed by the image retrieval engine 130 as described above.

At operation 204, the image process device 112 processes the retrieved images using various image processing techniques for further evaluation. These techniques are described in detail with reference to FIGS. 6-10.

At operation 206, the image process device 112 evaluates and determines whether at least one of the processed images represents the eye fundus of the subject being examined. If it is determined that none of the processed images is representative of the eye fundus ("NO" at operation 206), the operation of the image process device 112 returns to operation 202 to retrieve other images collected by the image capture device 110 and repeat the subsequent operations. If it is determined that at least one of the processed images is representative of the eye fundus ("YES" at operation 206), the image process device 112 performs operation 208.

In some embodiments, the operations 204 and 206 can be performed by the image evaluation engine 132 as described above.

At operation 208, the image process device 112 obtains the fundus image. In some embodiments, the image process device 112 can save at least one of the images that have been retrieved from the image capture device 110 if the image has one or more predetermined characteristics (e.g., desired image quality and/or size). Otherwise, the image process device 112 interfaces with the image capture device 110 to rapidly capture another image with the predetermined characteristics. For example, if the image process device 112 determines that the image retrieved from the image capture device 110 are of insufficient quality although the image has been determined to represent the eye fundus, the image process device 112 can trigger the image capture device 110 to capture another image of sufficient quality in real-time.

As the processed images have been already determined to be representative of the eye fundus as desired at operation 206, the image that is newly captured in real-time by the image capture device 110 remains representative of the eye fundus. Once the image process device 112 obtains a new fundus image of sufficient quality from the image capture device 110, the image process device 112 saves the new fundus image for subsequent use. In some embodiments, the operation 208 can be performed by the fundus image obtaining engine 134 as described above.

Figure 6:
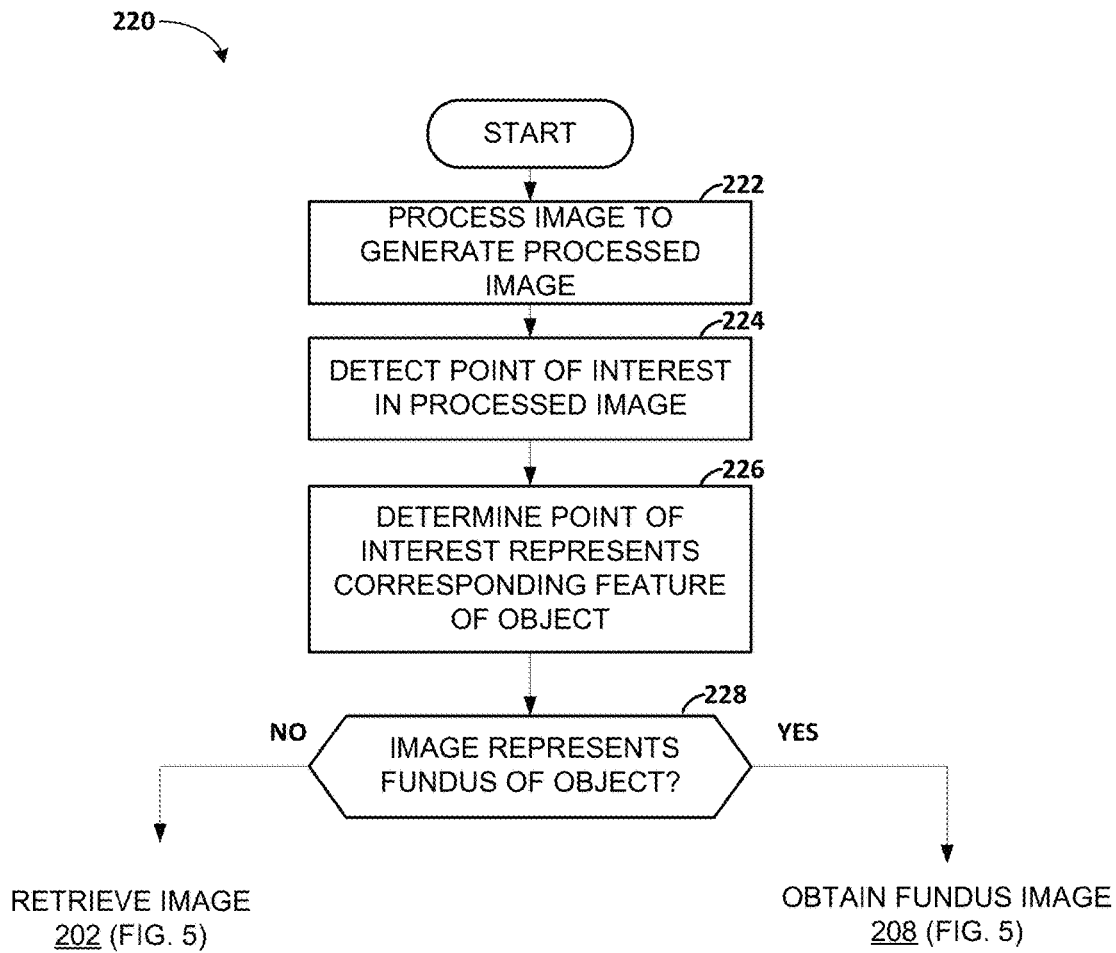
FIG. 6 is a flowchart illustrating an example method of operating an image evaluation engine.

FIG. 6 is a flowchart illustrating an example method 220 of operating the image evaluation engine 132.

In some examples, the image evaluation engine 132 can generally perform multiple steps for determining whether a fundus image that appropriately represents the eye fundus has been captured by the image capture device 110. The steps can include a preprocessing step, a feature detection step, and a result determination step. Examples of these steps are described in the following operations.

At operation 222 (e.g., the preprocessing step), the image evaluation engine 132 processes the images retrieved from the image capture device 110 and generates one or more processed images. An example of image processing performed in the operation 222 is described with reference to FIG. 7.

At operation 224 (e.g., the processing step), the image evaluation engine 132 operates to detect at least one point of interest in the processed images. The point of interest in the processed images is used to determine whether the processed images are representative of the fundus image. In some embodiments, the point of interest is any feature that can be identified from the processed images and is likely to be representative of a corresponding feature of the eye fundus. For examples, the point of interest can be selected as an area having a different intensity from surrounding areas or from the average intensity of the entire object. By way of example, the point of interest can be one or more solid circles identifiable from the processed images, one of which might correspond to the optic disc of the eye fundus. The point of interest can be selected in the processed images in various manners, as described in FIG. 9.

At operation 226 (e.g., the result determination step), the image evaluation engine 132 operates to determine whether the point of interest represents its corresponding feature of the eye fundus. Various methods can be used to perform the determination. In some embodiments, historical processing data can be used to determine that the point of interest selected from the processed image corresponds to a feature of the eye fundus. The historical processing data can be established based on the shape, size, and/or position of the feature of the eye fundus. Other methods can be used to perform the operation 226. One example uses a consistency of the point of interest in a plurality of processed images, and is described with reference to FIG. 11.

If it is determined that the point of interest matches the corresponding feature of the eye fundus, it is considered that the processed image is representative of the eye fundus. Otherwise, the processed image is determined to not represent the eye fundus.

At operation 228, if it is determined that the processed image represents the eye fundus ("YES" at the operation 228), the image process device 112 moves on to perform the operation 208. Otherwise ("NO" at the operation 228), the image process device 112 returns to the operation 202 to retrieve other images collected by the image capture device 110 and repeat the operations following the operation 202.

Figure 7:
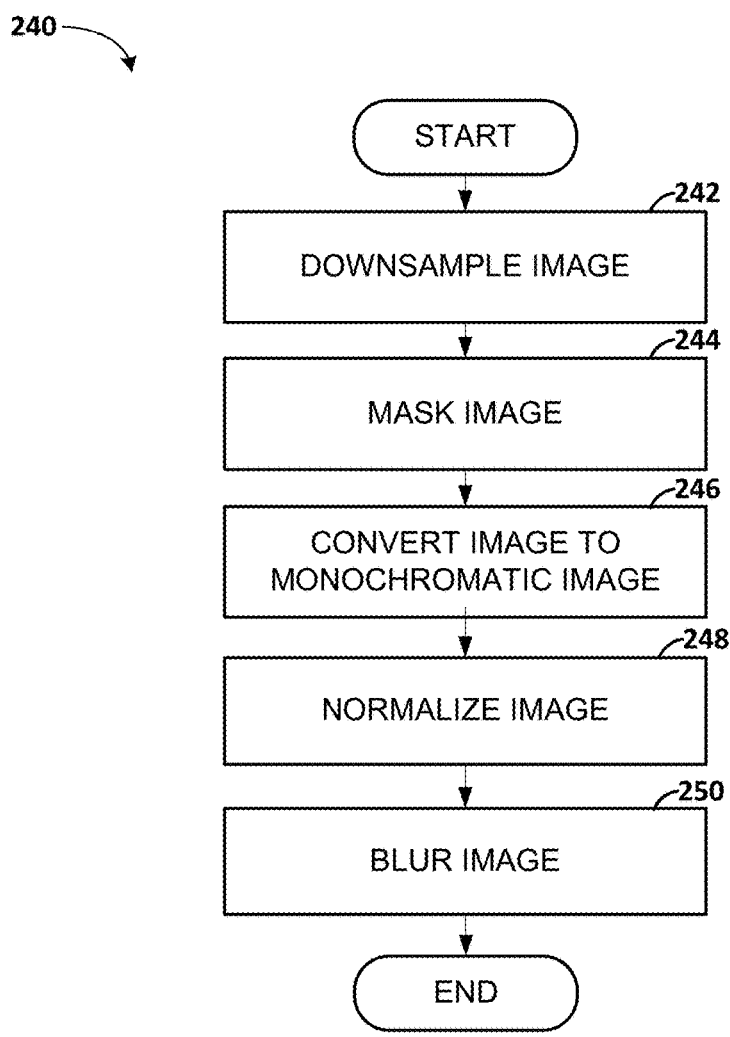
FIG. 7 is a flowchart illustrating an example method of performing an operation of the image evaluation engine.
Figure 8:
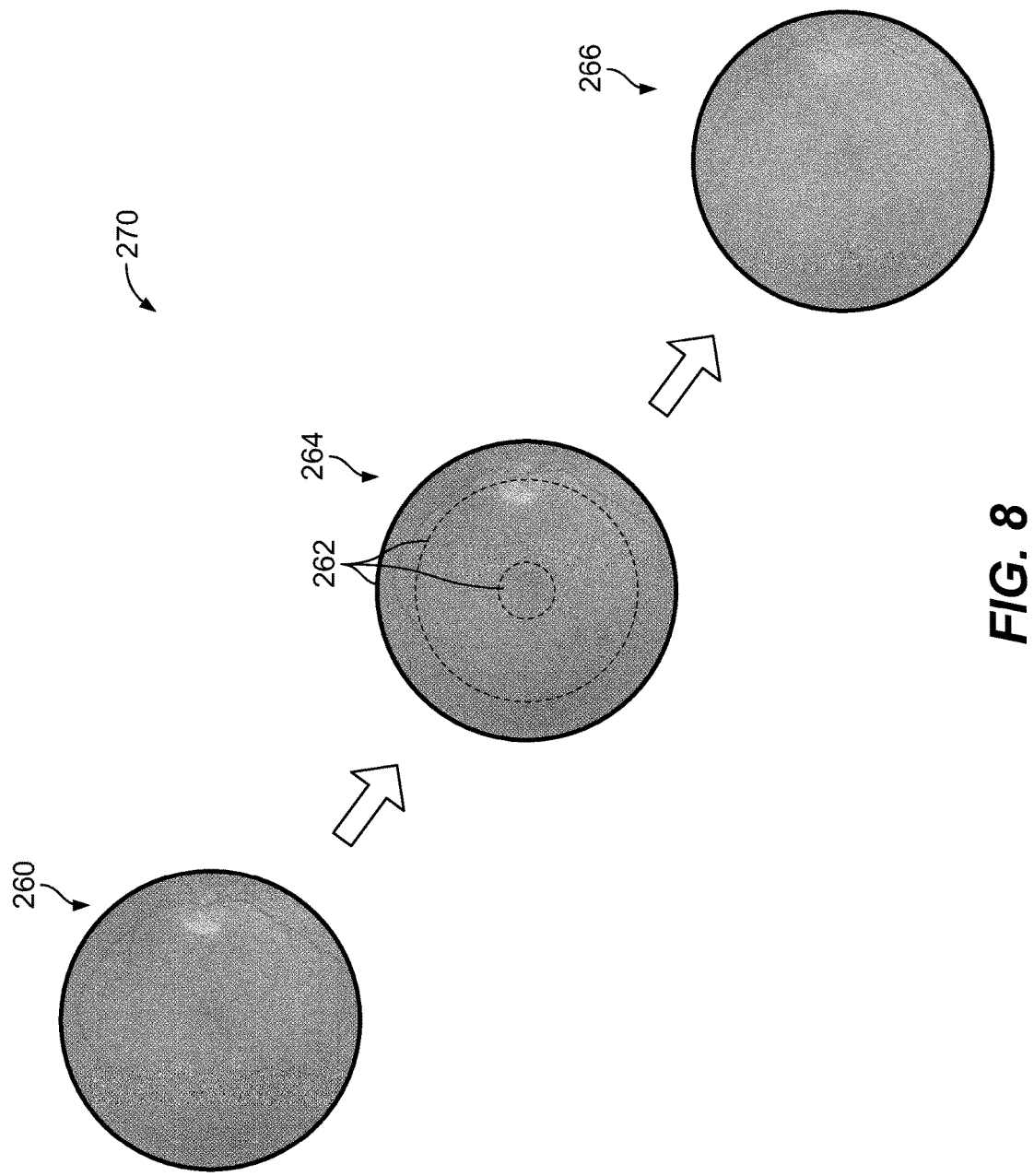
FIG. 8 illustrates example images that are processed by the image process device in the method of FIG. 7.

Referring to FIGS. 7 and 8, an example of the operation 222 of the image evaluation engine 132 of the image process device 112 is described in more detail.

FIG. 7 is a flowchart illustrating an example method 240 of performing the operation 222 of the image evaluation engine 132 of the image process device 112.

At operation 242, the image process device 112 can perform downsampling of the images retrieved from the image capture device 110. The downsampling of the images resizes the images. In some embodiments, the image process device 112 reduces the size of the images suitable for subsequent image processing.

At operation 244, the image process device 112 performs masking on the images to remove the surroundings of the object in the images, which are clearly not part of the eye fundus.

At operation 246, the image process device 112 converts the images to monochromatic images. Where the images retrieved from the image capture device 110 are three-channel color images, the images can be reduced to a single-channel image. In some embodiments, the images can be converted to a grayscale image. In other embodiments, the images can be reduced to a single-channel image in another color (e.g., red).

At operation 248, the image process device 112 normalizes the images to change the range of pixel intensity values of the images. In some embodiments, the intensity values of each image are stretched between possible minimum and maximum values.

At operation 250, the image process device 112 blurs at least one part of the image, using a kernel of a desired size, to remove noise.

In other embodiments, the operations 242, 244, 246, and 248 of the method 240 can be performed in different order. In yet other embodiments, the method 240 includes additional image processes. In yet other embodiments, the method 240 include only one or some of the operations 242, 244, 246, and 248.

FIG. 8 illustrates example images that are processed by the image process device 112 in the method 240 of FIG. 7.

One or more images 260 are collected by the image capture device 110. In some embodiments, the retrieved image 260 is a three-channel (R,G,B) color image. In other embodiments, the retrieved image 260 can be a single-channel color image, depending on the configuration of the image capture device 110. In yet other embodiments, the retrieved image 260 can have different hues. For example, the retrieved image 260 can have purple hue where the image capture device 110 uses an infrared camera.

The retrieved image 260 can be processed with a mask to eliminate a portion of the image 260 that is not interested for further image processing. As illustrated, in some embodiments, a set of concentric circles 262 can be used to define a boundary within the image 260 that includes an area possibly corresponding to the eye fundus. Once the image 260 is appropriately arranged relative to the concentric circles 262, the portion outside the boundary of the concentric circles 262 (e.g., an outmost circle) is removed, and only a portion of the image 262 within the concentric circles 262 (e.g., the outmost circle) remains as a masked image 264 and is used for subsequent processing.

The masked image 264 is then converted to a monochromatic image 266. In this example, the masked image 264 in three-channel colors is converted to a grayscale image. Other embodiments of the monochromatic image 266 can have different colors.

As discussed above, additional processes can be applied to the retrieved image 260 in various orders. In this document, the images processed in the operation 222 by the image process device 112 are referred to as a processed image 270.

Figure 9:
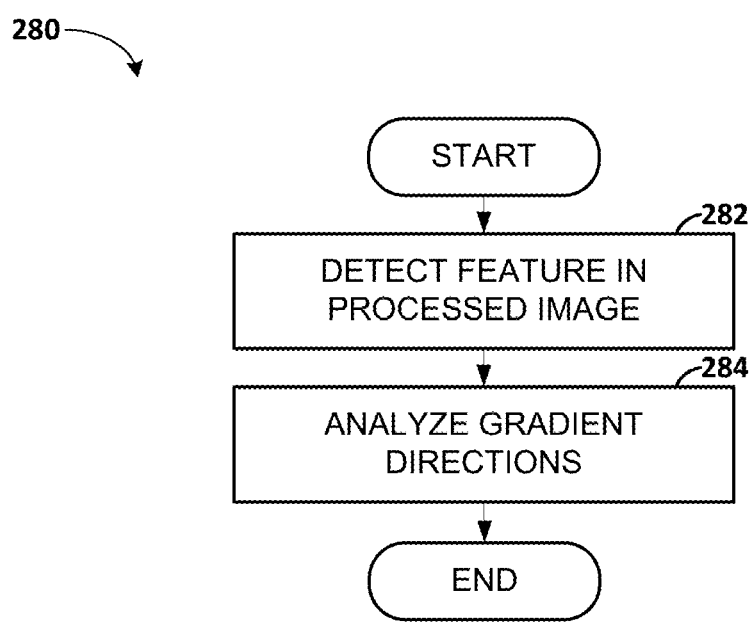
FIG. 9 is a flowchart illustrating an example method of performing an operation of the image evaluation engine.
Figure 10:
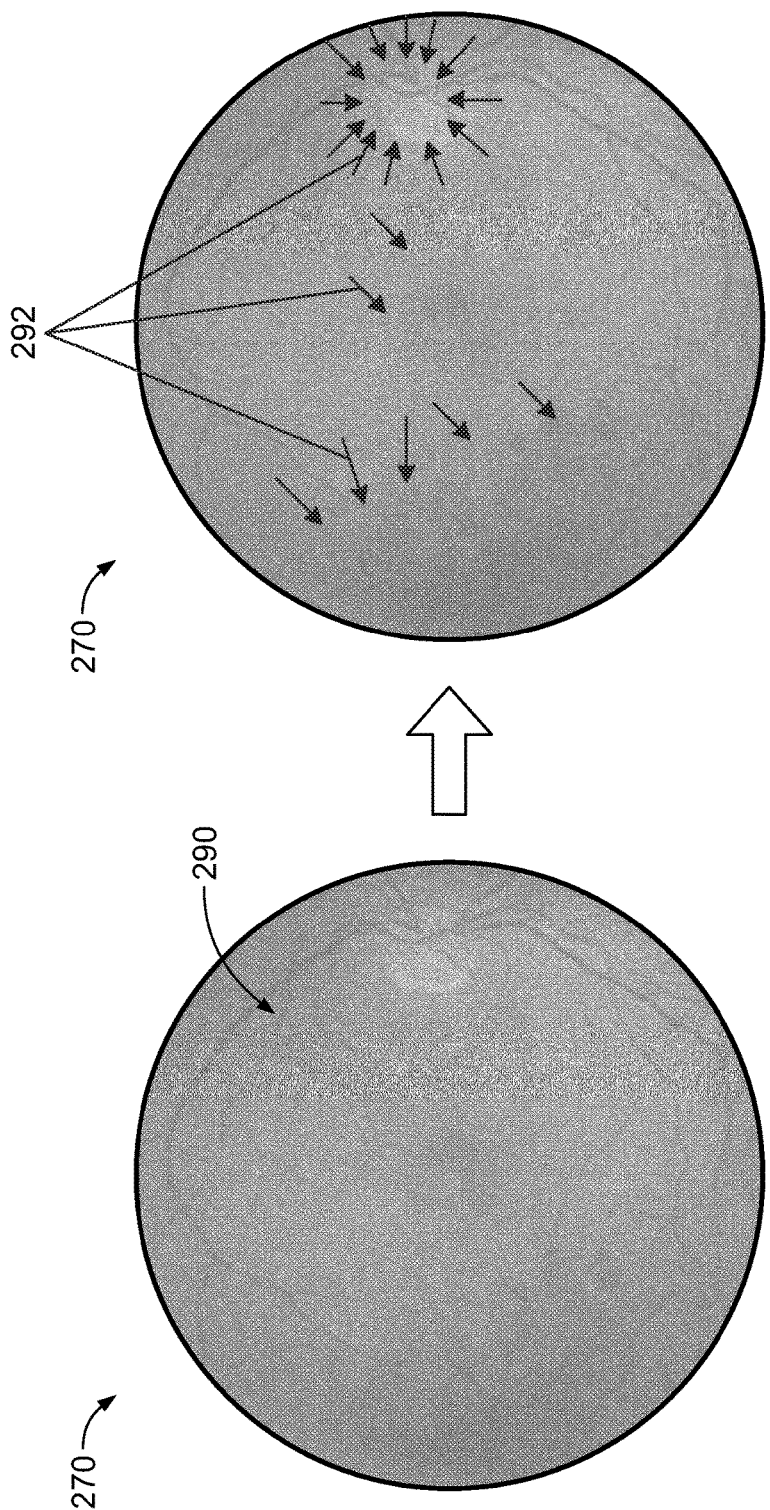
FIG. 10 illustrates example images that are processed by the image process device in the method of FIG. 9.

Referring to FIGS. 9 and 10, an example of the operation 224 of the image evaluation engine 132 of the image process device 112 is described. FIG. 9 is a flowchart illustrating an example method 280 of performing the operation 224 of the image evaluation engine 132 of the image process device 112. FIG. 10 illustrates example images that are processed by the image process device 112 in the method 280 of FIG. 9.

At operation 282, the image process device 112 operates to detect one or more features 292 (FIG. 10) within the processed image 270 to identify at least one point of interest for evaluation of the image. In some embodiments, the image process device 112 detects one or more circles within the processed image 270. By way of example, the image process device 112 finds a circle that would correspond to the optic disc of the eye. In other embodiments, the image process device 112 can consider other characteristics of the eye when detecting the features 292.

Various image processing methods can be used in the operation 282. In some embodiments, the image process device 112 uses edge detection to identify points in the processed images 270 at which the image brightness changes sharply or has discontinuities. The edge detection is executed to determine where feature edges are in the image. The image process device 112 can further perform contour tracing on the processed image 270 to create contours of the connected edges. In addition, some embodiments of the image process device 112 can execute ellipse fitting by fitting an ellipse around a contour or part of the contour. Other image processes can also be performed either additionally or alternatively.

At operation 284, the image process device 112 analyzes gradient directions in the processed image 270 after the operation 282. The gradient directions represent directional changes in the intensity in the processed image 270 and are used to extract the information about the features detected in the operation 282.

The image process device 112 can employ various image process methods in the operation 284. In some embodiments, the processed image 270 can be further blurred in addition to the blurring executed in the operation 250 above. The image process device 112 can find gradient directions in the image by creating vectors 292 (FIG. 10, which shows only a portion of example vectors on the image) in the direction of the gradient. The image process device 112 can then detect intersections of the vectors 292 to determine a point of interest in the processed image 270. In some embodiments, a position or area at which a certain number of vectors 292 intersect can be selected as a point of interest. By way of example, a point or area at which the highest number of vectors 292 intersect can represent a highest intensity value in the image and can be determined as a point of interest.

Figure 11:
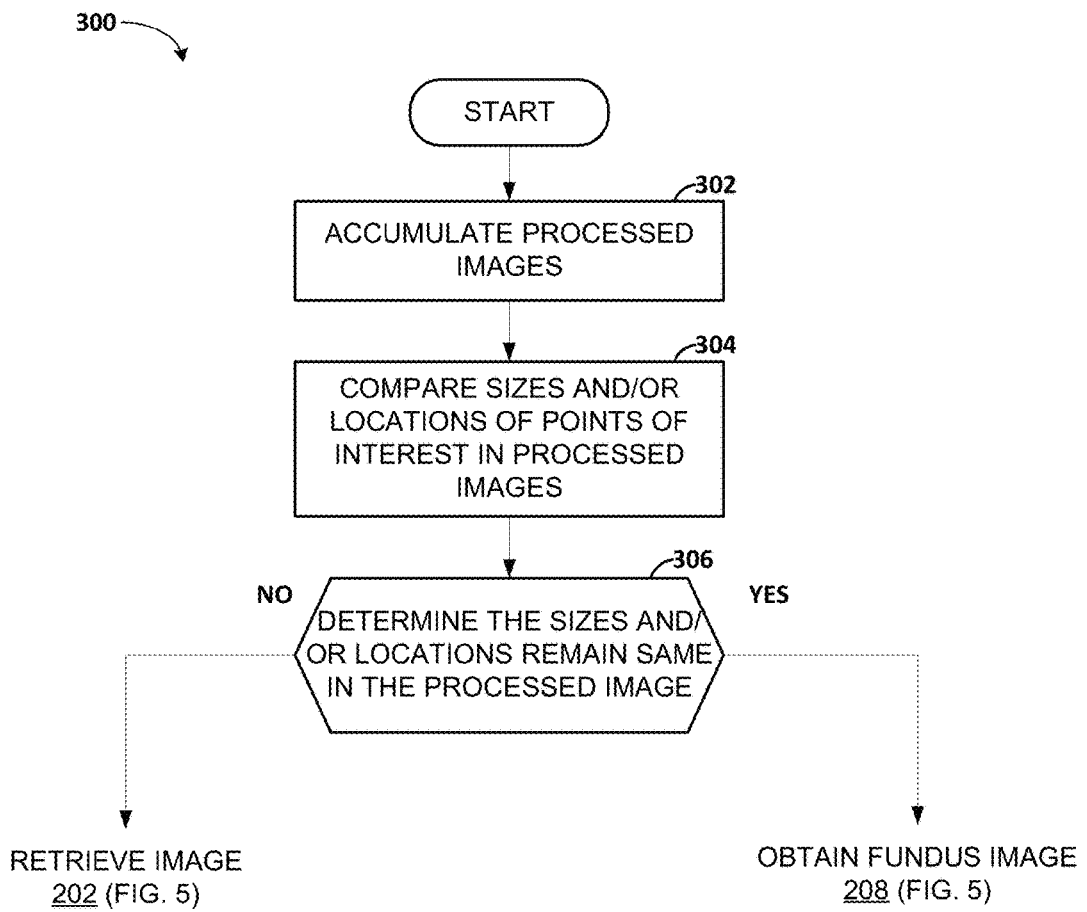
FIG. 11 is a flowchart illustrating an example method of performing an operation of the image evaluation engine.
Figure 12:
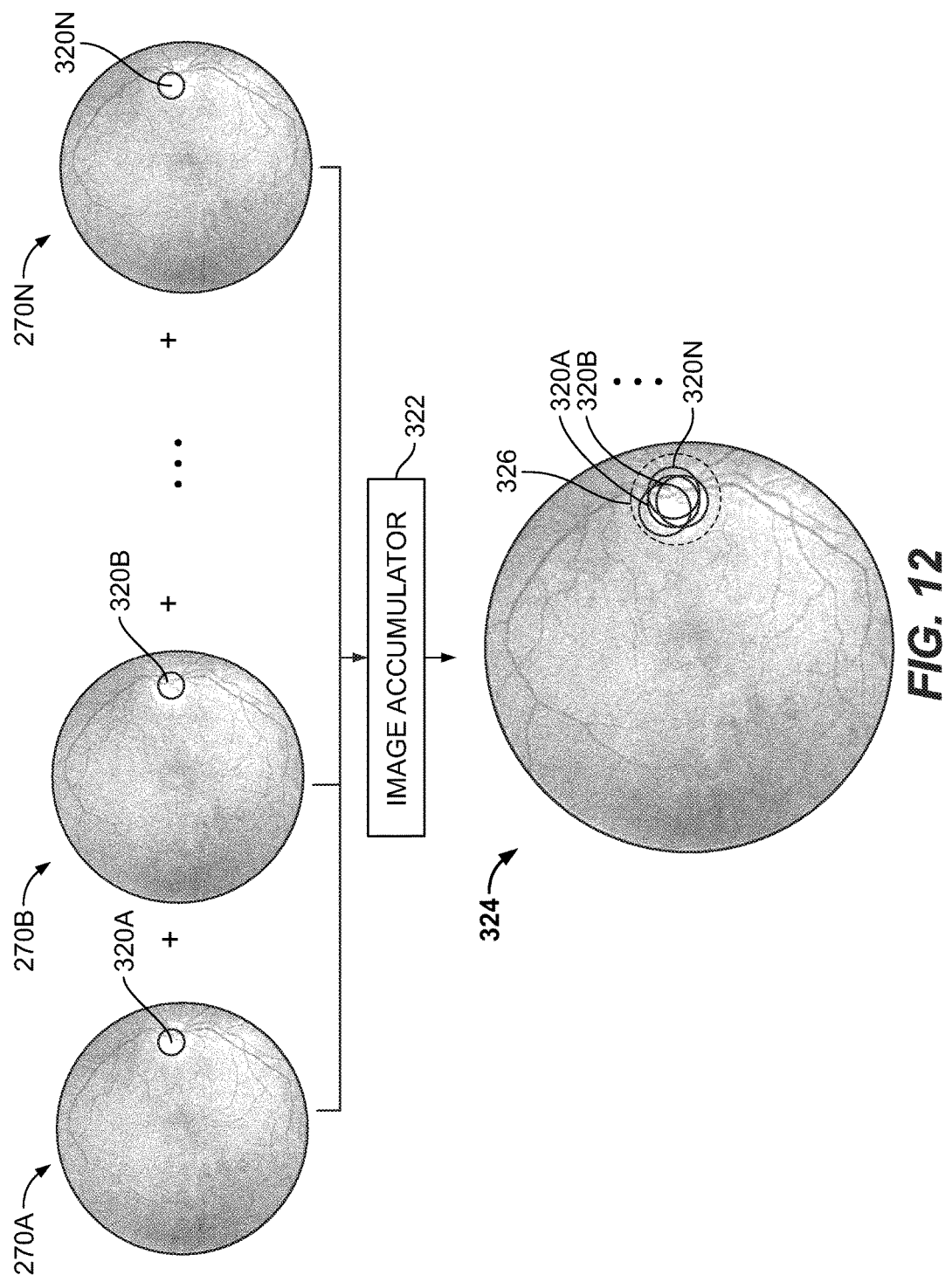
FIG. 12 illustrates example images that are processed by the image process device in the method of FIG. 11.

Referring to FIGS. 11 and 12, an example of the operation 226 of the image evaluation engine 132 of the image process device 112 is described. FIG. 11 is a flowchart illustrating an example method 300 of performing the operation 226 of the image evaluation engine 132 of the image process device 112. FIG. 12 illustrates example images that are processed by the image process device 112 in the method 300 of FIG. 11.

As described above, the method 300 is performed to evaluate whether the selected point of interest represents its corresponding feature of the eye, as opposed to something irrelevant to the eye fundus (e.g., glare and other artifacts). As illustrated in FIG. 12, the points of interest 320 (including 320A-320N) have been detected in the operation 224 above and can be evaluated whether they are representative of the optic disc of the eye fundus in the following operations.

At operation 302, the image process device 112 operates to accumulate a plurality of the processed images 270

(including 270A-270N) that have been processed in the operation 224, using an image accumulator 322. The image accumulator 322 of the image process device 112 operates to retrieve a predetermined number of the processed images 270 and accumulate them to generate an accumulated image 324. Accordingly, the points of interest 320 (including 320A-320N) that have been identified in the processed images 270 (including 270A-270N), respectively, are also incorporated in the accumulated image 324. By way of example, the image accumulator 322 generates an accumulated image 324 by taking a series of five of the processed images 270 where the images corresponding to the five processed images 270 were captured sequentially in 150 milliseconds by the image capture device 110. Other embodiments of the image accumulator 322 can operate in other manners. In yet other embodiments, the image accumulator 322 operates similarly to the capturing operation disclosed in U.S. patent application Ser. No. 14/633,601, titled THROUGH FOCUS RETINAL IMAGE CAPTURING, filed Feb. 27, 2015, the entirety of which is incorporated herein by reference to that extent that it does not conflict with the present disclosure.

At operation 304, the image process device 112 operates to compare the sizes and/or positions of the points of interest 320 (including 320A-320N) identified in the processed images 270, respectively.

At operation 306, it is determined whether the sizes and/or positions of the points of interest 320 remain substantially the same within the accumulate image 324 (e.g., among the processed images 270). In some embodiments, the sizes of the points of interest 320 are determined to remain the same if they are within a predetermined range in size. In some embodiments, a range of area 326 is defined to determine the consistency of the positions of the points of interest 320. By way of example, the range of area 326 is a circle with a predetermined diameter. In some embodiments, if all of the points of interest 320 are within the range of area 326, it is considered that the points of interest 320 remain stable among the processed images 270. In other embodiments, if at least a predetermined number of the points of interest 320 are within the range of area 326, it is considered that the points of interest 320 are consistently located.

If it is determined that the locations of the points of interest 320 remain the same ("YES" at the operation 306), it is considered that the set of the points of interest 320 represents its corresponding feature of the eye fundus, and, therefore, the processed images 270 represent the fundus image as desired. Then, the operation 208 is subsequently performed. In this illustration, the points of interest 320 are determined to match the optic disc of the eye fundus.

If it is not determined that the locations of the points of interest 320 remain the same ("NO" at the operation 306), the processed images 270 are determined to not represent the eye fundus, and the image process device 112 returns to the operation 202 to retrieve other images collected by the image capture device 110 and repeat the operations following the operation 202.

Figure 13:
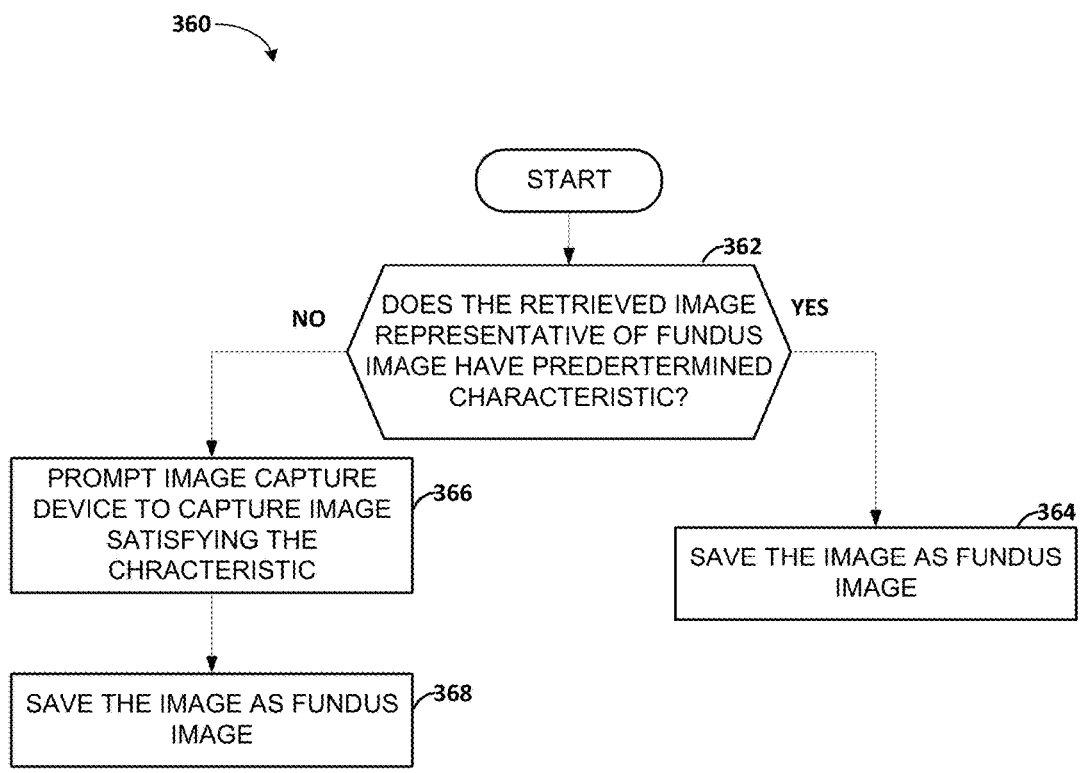
FIG. 13 is a flowchart illustrating an example method of performing an operation of FIG. 5.

FIG. 13 is a flowchart illustrating an example method 360 of performing the operation 208 of FIG. 5.

As described above, the operation 208 is to obtain a desired fundus image based on the determination made in the operation 206. In some embodiments, the operation 208 is performed by the fundus image obtaining engine 134.

In some applications, the images first collected by the image capture device 110 are of low quality for speeding up the operation of the system 100 (including the fundus image capture system 102), improving the efficiency thereof, and various other reasons. Therefore, at least some of these images do not have sufficient characteristics (e.g., a sufficient image quality and/or size) for the user U (e.g., a caregiver and medical professional) to review for diagnostic or other purposes, although the images have captured the fundus image correctly. In this case, the image capture device 110 needs to capture another image of sufficient characteristics while collecting the same fundus image.

At operation 362, the image process device 112 determines whether at least one of the images 260, which were originally retrieved from the image capture device 110 and correspond to the processed images 270 that have been determined to represent the eye fundus, has one or more predetermined characteristics that meet a threshold. Examples of the characteristics include an image quality and an image size. The image quality can be determined in terms of an image resolution. In addition or alternatively, the image quality is determined in terms of at least one of sharpness, noise, dynamic range, tone reproduction, contrast, color accuracy, distortion, vignetting, exposure accuracy, lateral chromatic aberration, lens flare, color moire, and artifacts.

By way of example, the image process device 112 determines whether the retrieved image 260 has an image resolution that is above a predetermined level. If the image 260 has such an image resolution, the image 260 is considered to be a desired fundus image.

If it is determined that the retrieved image 260 has the predetermined characteristics ("YES" at the operation 362), the method 360 moves on to operation 364. At operation 364, the image process device 112 saves the retrieved image 260 as a desired fundus image for subsequent use (e.g., for the user U's review).

If it is determined that the retrieved image 260 does not have the predetermined characteristics ("NO" at the operation 362), the method 360 continues at operation 366.

At the operation 366, the image process device 112 prompts the image capture device 110 to rapidly capture another image that satisfies the threshold of the characteristics. In some embodiments, the image process device 112 communicates with the image capture device 110 to enable the image capture device 110 to adjust at least one of the settings (e.g., brightness level) so that the next image frame is of better quality. As the entire process of the image process device 112 is performed in a short period of time, the newly captured image is still representative of the eye fundus. As the image process device 112 automatically triggers the image capture device 110 to capture an image without receiving a user interaction (e.g., a triggering action), the fundus image capture system 102 can obtain a fundus image of desired quality without delay and/or shaking due to the user interaction.

At the operation 368, similarly to the operation 364, the image process device 112 saves the new image of sufficient characteristics as a fundus image for subsequent use.

Figure 14:
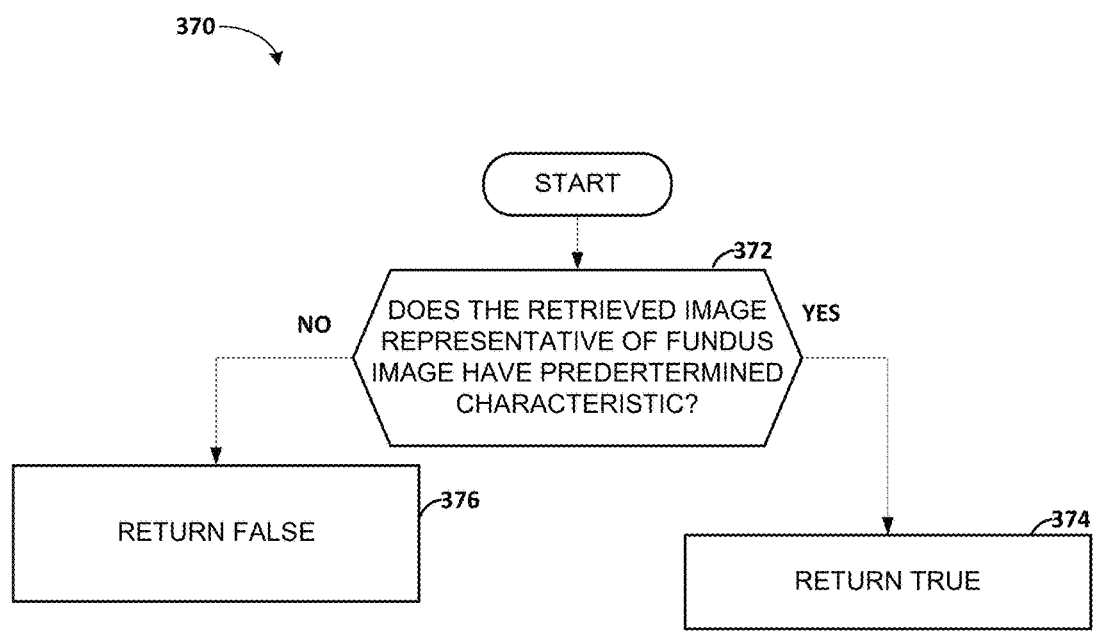
FIG. 14 is a flowchart illustrating another example method of performing the operation of FIG. 5

FIG. 14 is a flowchart illustrating another example method 370 of performing the operation 208 of FIG. 5. In some embodiments, the method 370 is similar to the method 360, and therefore, the description of the method 360 is incorporated by reference for the method 370 to the extent that it is compatible. In the method 370, the image process device 112 is not configured to control the image capture device 110 to capture another image.

Similarly to the operation 362, the operation 372 is performed to determine whether the image that has been determined to represent the eye fundus has one or more predetermined characteristics that meet a threshold.

Examples of the characteristics include an image quality and an image size. The image quality can be determined in terms of an image resolution. In addition or alternatively, the image quality is determined in terms of at least one of sharpness, noise, dynamic range, tone reproduction, contrast, color accuracy, distortion, vignetting, exposure accuracy, lateral chromatic aberration, lens flare, color moire, and artifacts.

If it is determined that the image has the predetermined characteristics ("YES" at the operation 372), the method 370 moves on to operation 374. At operation 374, the image process device 112 (e.g., the fundus image obtaining engine 134) returns TRUE value, which is to indicate that the image has the predetermined characteristics and that the field of view and optic disc position are achieved. Based on the return of TRUE value, the system can save the image as a fundus image. In other embodiments, the system can perform different actions upon receiving the output of TRUE value.

If it is determined that the image does not have the predetermined characteristics ("NO" at the operation 360), the method 360 continues at operation 376, in which the image process device 112 (e.g., the fundus image obtaining engine 134) returns FALSE value. Upon receiving FALSE output, the system can be configured to perform no further action. In other embodiments, the system can be configured to perform other actions when receiving the FALSE output.

Figure 15:
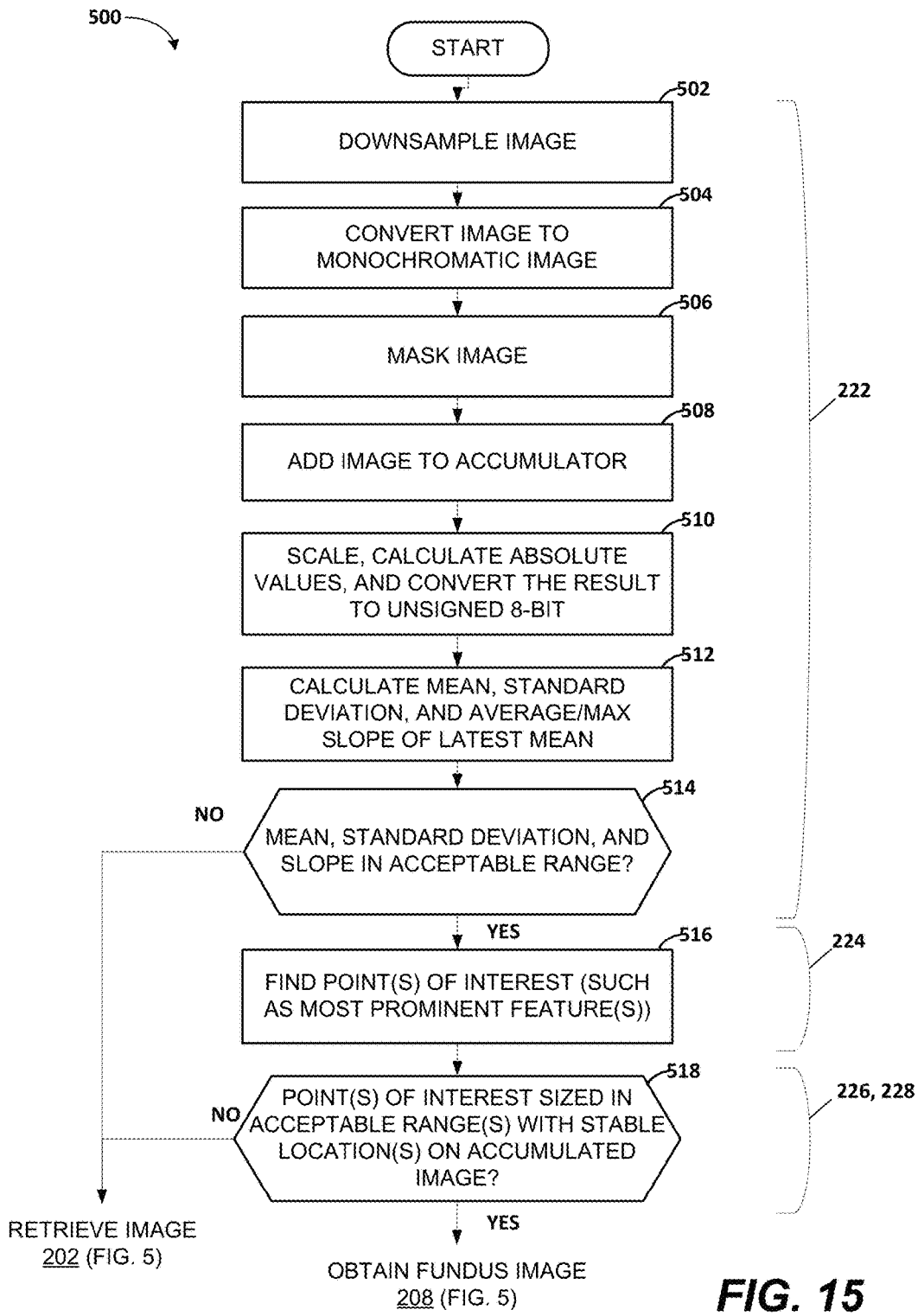
FIG. 15 is a flowchart illustrating another example method of operating the image evaluation engine.

FIG. 15 is a flowchart illustrating another example method 500 of operating the image evaluation engine 132. At least some of the steps included in the method 500 correspond to at least some of the steps of the method 220, as described in FIG. 6.

At operation 502, the image processing device 112 can perform downsampling of an image that is retrieved from the image capture device 110. The downsampling of the image resizes the image. In some embodiments, the image process device 112 reduces the size of the image suitable for subsequent image processing.

At operation 504, the image process device 112 converts the image to a monochromatic image. Where the image retrieved from the image capture device 110 is a three-channel color image, the image can be reduced to a single-channel image. In some embodiments, the image can be converted to a grayscale image. In other embodiments, the image can be reduced to a single-channel image in another color (e.g., red).

At operation 506, the image process device 112 performs masking on the image to remove the surroundings of the object in the image, which are clearly not part of the eye fundus. In some embodiments, the masking is calculated on an image that is scaled, cropped, and grayscaled.

At operation 508, the image process device 112 operates to add the image to an accumulator. In some embodiments, the accumulator at this operation is the image accumulator 322, and the operation 508 is executed similarly to the operation 302 as described in FIG. 11. In some embodiments, images that are scaled, cropped, and grayscaled are accumulated for subsequent processing.

At operation 510, the image process device 112 converts the accumulated image result from 32-bit floating point values to unsigned 8-bit for efficiency of further processing operations. Where the image processing performed by the image process device 112 is developed with OpenCV, the operation 510 can be implemented with "convertScaleAbs" function.

At operation 512, the image process device 112 operates to calculate a mean and standard deviation of array elements associated with the image, and further an average and/or maximum slope of the latest mean. These values help point to the presence of a fundus versus any other real world scenario the camera may encounter where the values would be less consistently range-bound. In OpenCv library, such a mean and standard deviation can be implemented with "meanStdDev" function.

At operation 514, the image process device 112 operates to determine whether the mean, standard deviation, and slope that are calculated in the operation 512 is within an acceptable range that is calculated by collecting a plurality of different fundus images and analyzing their means, slopes, and deviations. For example, a success criteria for the operation 512 is if the mean value is greater than 40 and less than or equal to 52, with a standard deviation to mean ratio of less than 0.1. If it is determined that they are in the acceptable range ("YES" at the operation 514), the method 500 moves on to operation 516. Otherwise ("NO" at the operation 514), the method 514 returns to the operation 202.

In some embodiments, the operations 502, 504, 506, 508, 510, and 512 correspond to the operation 222 of FIG. 6.

At operation 516, the image process device 112 operates to find one or more points of interest from the image. In some embodiments, the operation 516 corresponds to the operation 224 of FIG. 6. The point of interest is used to further determine whether the image is representative of the fundus image. In some embodiments, the most prominent feature in the image is selected as a point of interest. Multiple features can be selected as points of interest.

At operation 518, the image process device 112 operates to determine whether the points of interest found in a plurality of images are sized in acceptable ranges and positioned in stable locations versus corresponding key points on the accumulated image (such as the accumulated image 324). For example, it is configured such that the optic disc size in the latest image should meet the predetermined size of 7 pixels+/−50% tolerance, not more than two pixels larger than the optic disc in the accumulated image, as well as be within 1 pixel of the accumulated disc's location. If it is determined that the points of interest are within the acceptable size ranges and locations ("YES" at the operation 518), the method 500 moves on to perform the operation 208. Otherwise ("NO" at the operation 518), the method 500 returns to the operation 202. In some embodiments, the operation 518 corresponds to the operations 226 and 228 of FIG. 6.

In some examples of the method 500, analysis of gradient directions (such as the operation 284 in FIGS. 9 and 10) is not utilized.

FIG. 16 illustrates an exemplary architecture of a computing device that can be used to implement aspects of the present disclosure, including the fundus image capture system 102 (or the image capture device 110, the image process device 112, and/or the display device 114, separately), the control server 104, and the network 106, and will be referred to herein as the computing device 400. The computing device 400 is used to execute the operating system, application programs, and software modules (including the software engines) described herein.

The computing device 400 includes, in some embodiments, at least one processing device 402, such as a central processing unit (CPU). A variety of processing devices are available from a variety of manufacturers, for example, Intel or Advanced Micro Devices. In this example, the computing device 400 also includes a system memory 404, and a system bus 406 that couples various system components including the system memory 404 to the processing device 402. The system bus 406 is one of any number of types of bus structures including a memory bus, or memory controller; a peripheral bus; and a local bus using any of a variety of bus architectures.

Examples of computing devices suitable for the computing device 400 include a desktop computer, a laptop computer, a tablet computer, a mobile device (such as a smart phone, an iPod® mobile digital device, or other mobile devices), or other devices configured to process digital instructions.

The system memory 404 includes read only memory 408 and random access memory 410. A basic input/output system 412 containing the basic routines that act to transfer information within computing device 400, such as during start up, is typically stored in the read only memory 408.

The computing device 400 also includes a secondary storage device 414 in some embodiments, such as a hard disk drive, for storing digital data. The secondary storage device 414 is connected to the system bus 406 by a secondary storage interface 416. The secondary storage devices and their associated computer readable media provide nonvolatile storage of computer readable instructions (including application programs and program modules), data structures, and other data for the computing device 400.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 414 or system memory 404, including an operating system 418, one or more application programs 420, other program modules 422, and program data 424.

In some embodiments, computing device 400 includes input devices to enable a user to provide inputs to the computing device 400. Examples of input devices 426 include a keyboard 428, pointer input device 430, microphone 432, and touch sensitive display device 440. Other embodiments include other input devices 426. The input devices are often connected to the processing device 402 through an input/output interface 438 that is coupled to the system bus 406. These input devices 426 can be connected by any number of input/output interfaces, such as a parallel port, serial port, game port, or a universal serial bus. Wireless communication between input devices and input/output interface 438 is possible as well, and includes infrared, BLUETOOTH® wireless technology, 802.11a/b/g/n, cellular, or other radio frequency communication systems in some possible embodiments.

In this example embodiment, a touch sensitive display device 440 is also connected to the system bus 406 via an interface, such as a video adapter 442. The touch sensitive display device 440 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the touch sensitive display device 440, the computing device 400 can include various other peripheral devices (not shown), such as speakers or a printer.

When used in a local area networking environment or a wide area networking environment (such as the Internet), the computing device 400 is typically connected to the network through a network interface, such as a wireless network interface 446. Other possible embodiments use other communication devices. For example, some embodiments of the computing device 400 include an Ethernet network interface, or a modem for communicating across the network.

The computing device 400 typically includes at least some form of computer-readable media. Computer readable media includes any available media that can be accessed by the computing device 400. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 400.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Figure 17:
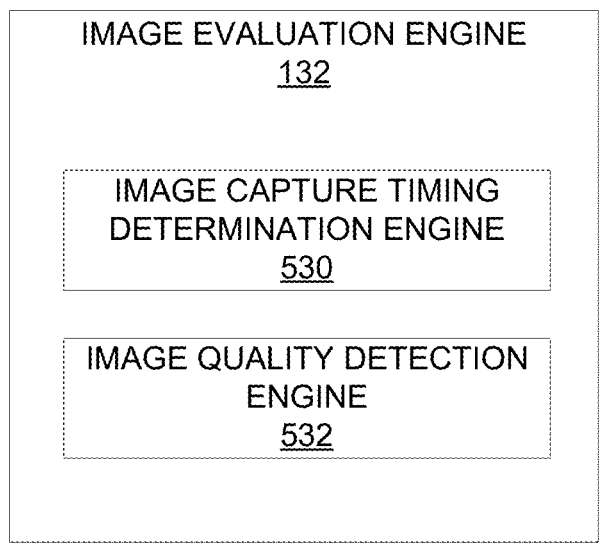
FIG. 17 illustrates another example of functional aspects of the image evaluation engine.

FIG. 17 illustrates another example of functional aspects of the image evaluation engine 132 of the image processing device 112. In this example, the image evaluation engine 132 includes an image capture timing determination engine 530 and an image quality detection engine 532. To clarification herein, a single image from the image capture device 110 can also be referred to herein as a frame or an image frame.

The image capture timing determination engine 530 operates to determine when a fundus camera (i.e., the image capture device 110) should capture a fundus image. In some embodiments, the image capture timing determination engine 530 receives sequential images (also referred to as image frames), evaluate the images, and output a suggested image capture setting, such as illumination setting. In some embodiments, the image capture timing determining engine 530 returns a number for a suggested illumination setting. When returning a nonzero value, the image capture timing determination engine 530 indicates that the image capture device 110 should capture an image. In general, the image capture setting or illumination setting is determined based on intensity values and the existence of stable features within the input images. An example method for such determination is described in more detail with reference to FIG. 18.

The image quality detection engine 532 operates to score images passed thereto based on focus quality. In some embodiments, the image quality detection engine 532 computes a decimal-precision score, representing the quality of the focus of a given image.

In some embodiments, the image capture timing determination engine 530 and the image quality detection engine 532 can be implemented using off-the-shelf software units, such as Python and OpenCV. The interpreter provided in Python is compiled for the fundus camera operating system to be able to run the engines, such as the image capture timing determination engine 530 and the image quality detection engine 532. Additional Python modules can be utilized in the implementation, such as NumPy (a scientific computing package that is used for data structuring and mathematical calculations) and OpenCV (when compiling OpenCV, a Python module can be part of the output for inclusion). OpenCV is the Open Computer Vision library that implements various computer vision algorithms utilized by, for example, the image capture timing determination engine 530 and the image quality detection engine 532. Such algorithms can include resizing, grayscaling, edge detection, feature detection, and other desirable image processing.

Figure 18:
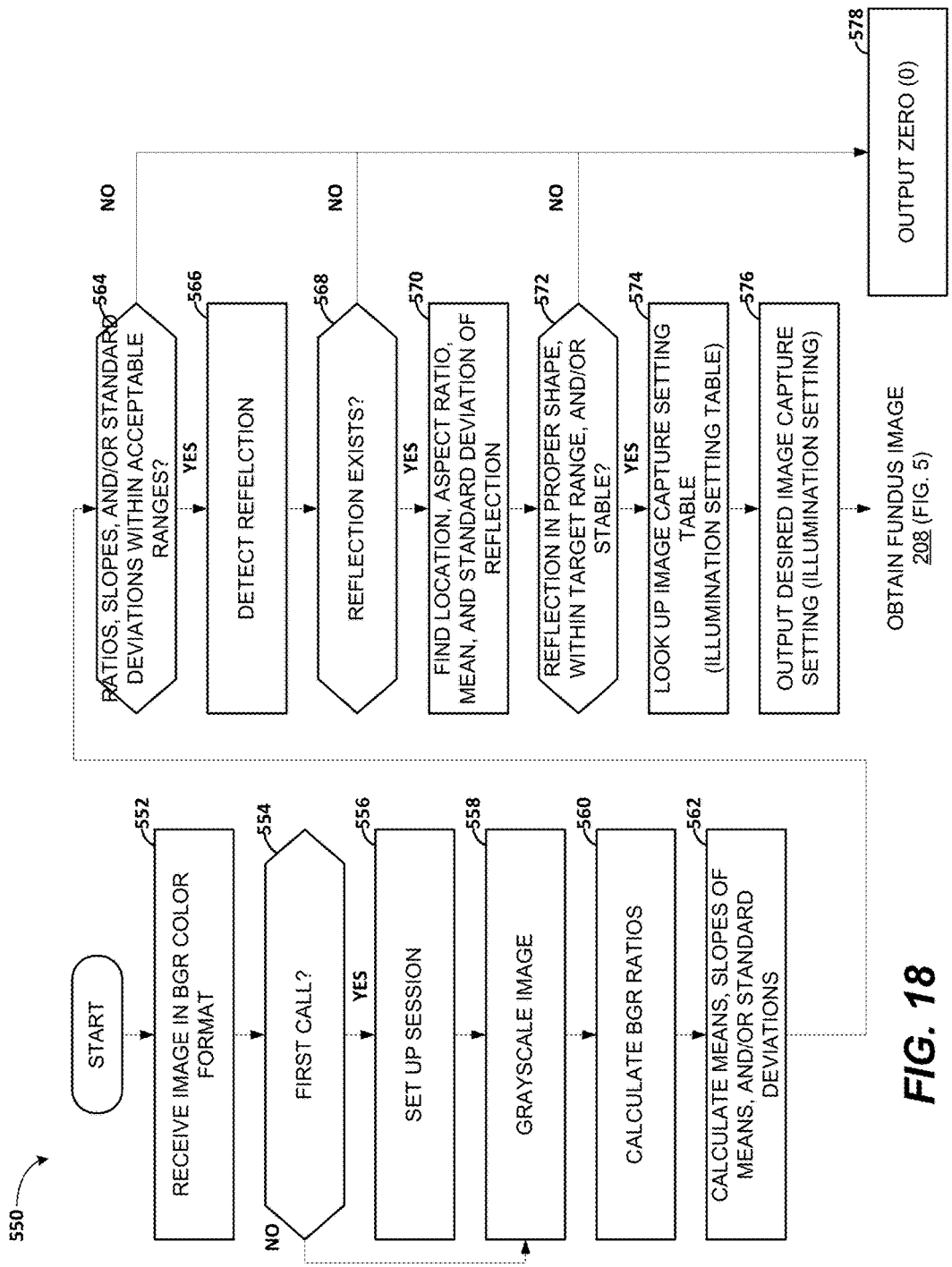
FIG. 18 is a flowchart illustrating an example method of operating an image capture timing determination engine of FIG. 17.

FIG. 18 is a flowchart illustrating an example method 550 of operating the image capture timing determination engine 530 of FIG. 17.

In general, the image capture timing determination engine 530 receives a buffer of image data and makes a determination about whether the image data represents a clear and stable view of the fundus from the perspective of the fundus camera. The image is analyzed on the colors, intensities, and features present in each image. Further, the image is evaluated to detect such items (i.e., the colors, intensities, and features) change over time. When the image capture timing determination engine 530 determines that the fundus camera is in a desired position to capture a quality image, the image capture timing determination engine 530 can output a desired image capture setting. In some embodiments, such a desired image capture setting includes a numerical value suggesting illumination duration to use. When it is not determined that the fundus camera is in the desired position, the image capture timing determination engine 530 can output a value of zero (0), which indicates the fundus camera is not ready for image capturing. Accordingly, the image capture timing determination engine 530 can predict when a quality image of the fundus can be captured. Instability in the intensities and features of the image frames can introduce motion blur, or the fundus camera can become out of position during capture. Further, without a proper distance (e.g., z-axis distance) of the fundus camera away from the eye, illumination levels in the resulting images can be insufficient.

A fundus camera in the image capture device 110 can be of various types. In the illustrated example, the fundus camera can include the RetinaVue Network, available from Welch Allyn, Inc. (Skaneateles Falls, N.Y.).

At operation 552, the image capture timing determination engine 530 can receive a buffer of image data corresponding to one or more images. In some embodiments, the image capture timing determination engine 530 is called with parameters of an image buffer and the integer 1. The image buffer is used for processing, and the integer 1 is used to indicate that the image capture timing determination engine 530 should control its own session.

In some embodiments, the images are in BGR color format. The images can be of different dimension. In some embodiments, the images have 160×120 pixels. As described, the image capture timing determination engine 530 operates to detect an infrared illuminated fundus.

At operation 554, it is determined whether the current session is the first call. If so ("YES" at the operation 554), the method 550 moves on to operation 556. Otherwise ("NO" at the operation 554), the method 550 skips to operation 558.

At operation 556, the image capture timing determination engine 530 operates to set up the session. In some embodiments, the image capture timing determination engine 530 maintains the notion of a session or a state machine that is created and destroyed as the process is stopped or started. When the session is started, various initial calculations are done based on the inputted image frame properties. One example of such calculations is to obtain an area of interest that the image capture timing determination engine 530 further processes. The area of interest is then converted into a mask to isolate those pixels.

At operation 558, the image capture timing determination engine 530 converts the image frame to a grayscaled image. Where the image frame is in BGR format, the image capture timing determination engine 530 converts the 3-channel image frame to a one-channel grayscale. The grayscaled image is stored in memory for later use.

During operations 560 and 562, the image capture timing determination engine 530 operates to determine whether the image passed is one of a fundus. By contrast to any other real world scenario, a properly aligned fundus appears with a smooth purple background from the infrared illumination. If the intensities and color ratios of the original frame fall within a predetermined value and are thus considered stable, the image capture timing determination engine 530 proceeds with further steps. If is fundus image is not recognized to be stable, the image capture timing determination engine 530 skips further processing and returns.

In particular, at the operation 560, the image capture timing determination engine 530 calculates BRG ratios. One of the measurements used to identify a fundus is the color ratios of the inputted image's area of interest. In some embodiments, the blue-green and red-blue ratios are used to match with the expected fundus color range.

At the operation 562, the image capture timing determination engine 530 calculates means of grayscale intensities, slopes of the means, and/or standard deviations. The mean is computed for each image frame and prior values are stored to enable calculation for the slope. The slope of the mean grayscale intensities for each frame is used to indicate temporal stability of the fundus view. A larger slope points to image instability. The standard deviation of the grayscale intensities contributes to information about the spatial stability of the fundus. The standard deviation can be a high value in the dark or when there is movement, such as when a user is navigating the camera into the eye. Similarly to the mean, previous values of standard deviations are stored for further computation.

At operation 564, it is determined whether the ratios, the slopes, and/or the standard deviations fall within acceptable ranges. In the illustrated embodiment, all of the ratios, the slopes, and the standard deviations are considered together. If any of the ratios, the slopes, and the standard deviations is outside the acceptable ranges ("NO" at the operation 564), the method 550 ends at operation 578, in which the image capture timing determination engine 530 outputs a value of zero (0) to indicate the fundus camera is not ready for image capturing. If all of the ratios, the slopes, and the standard deviations fall within the acceptable ranges ("YES" at the operation 564), the method 550 continues on at operation 566. In other embodiments, however, only one of the ratios, the slopes, and the standard deviations is considered for the determination at the operation 564. In yet other embodiments, any combination of the ratios, the slopes, and the standard deviations are considered for the determination.

At operation 566, the image process device 112 detects a reflection on a screen of the fundus camera. In some embodiments, when the proper alignment and distance (e.g., z-axis distance) from the fundus is achieved, a white reflection appears on the screen of the fundus camera. The image capture timing determination engine 530 can use this reflection marker as part of the image capture criteria. In some embodiments, as the z-axis distance is adjusted, the reflection turns from a focused square shape (when the camera is further from the eye) to a large blurry blob (when the camera is closer to the eye). The image capture timing determination engine 530 looks for a predetermined aspect ratio of the reflection. Similar to the fundus detection operations above, when the reflection marker is not stable, the image capture timing determination engine 530 waits until the reflection marker is stabilized before capturing an image.

In some embodiments, the reflection marker needs to appear within a predetermined area of the screen for the image capture timing determination engine 530 to trigger. In some embodiments, the shape of the area surrounds the best location for proper illumination of the eye during capture. An example of the shape is a top-heavy diamond.

In some embodiments, to detect the reflection in an image that is considered to have a stable view of the fundus, the image capture timing determination engine 530 can compute the difference of multiple image frames. The differences are then combined using a bitwise AND function, which takes two binary representations and performs the logical AND operation on each pair of the corresponding bits by multiplying them. This combination can extract any changes from the stable background, as when the reflection appears and moves. The number of frames used determines how much noise is removed from the result. However, the number of frames used should be limited, because a large number of frames can erode the reflection itself. The final check is to determine whether the location of maximum intensity in the added image corresponds to a minimum intensity value in the current frame.

At operation 568, it is determined whether a reflection exists on the screen. If so ("YES" at the operation 568), the method 550 moves on to operation 570. Otherwise ("NO" at the operation 568), the method 550 ends at operation 578, in which the image capture timing determination engine 530 outputs a value of zero (0) to indicate the fundus camera is not ready for image capturing.

At operation 570, the image capture timing determination engine 530 finds a location, an aspect ratio, a mean, and a standard deviation of the reflection.

In some embodiments, the shape of the target area to which the user needs to move the reflection is predetermined by coordinates when the image capture timing determination engine 530 is implemented. Such coordinates are inputted to a function that determines if the current location of the reflection is inside of the coordinates.

In some embodiments, the image capture timing determination engine 530 requires two image frames with a reflection to trigger. The current and previous locations are stored to measure how much the reflection has moved between the frames. A distance greater than a predetermined threshold can indicate that the reflection is unstable.

The aspect ratio and size of the detected reflection is also analyzed. In some embodiments, the image capture timing determination engine 530 looks for a predetermined shape, such as a shape that is somewhat round but not vertical. As the reflection becomes more round, the reflection grows in size. Thus, the area of the detected reflection cannot be too large.

In some embodiments, the image capture timing determination engine 530 operates to exclude an undesirable reflection from the analysis above. When approaching the eye with an infrared camera, the IR light enters the eye and reflects out, similarly to the red eye reflection found in photographs. To not confuse such IR reflection with the desired reflection, the image capture timing determination engine 530 checks the surrounding intensities for a pattern that would be indicative of an external eye. A line extending across the brightest point in the image can be measured. If the intensities form two maximum peaks with a dip in-between, the reflection can be ignored since the desired reflection tends to form only one peak.

At operation 572, the image capture timing determination engine 530 determines whether the reflection has the predetermined shape, is located with within the target range, and/or is stable. If so ("YES" at the operation 572), the method 550 continues on at operation 572. Otherwise ("NO" at the operation 572), the method 550 ends at operation 578, in which the image capture timing determination engine 530 outputs a value of zero (0) to indicate the fundus camera is not ready for image capturing.

At operation 574, the image capture timing determination engine 530 looks up an image capture setting table. From the table, the image capture timing determination engine 530 determines a desired image capture setting, such as an illumination setting. The image capture timing determination engine 530 can select such a desired image capture setting based on one or more criteria. In some embodiments, the image capture timing determination engine 530 selects the desired image capture setting based on the mean intensity of the IR light in the input image frame.

Since the image capture timing determination engine 530 analyzes an illuminated view of a fundus, the image capture timing determination engine 530 can make a suggestion to the system about the duration of white light that is used for image capture. The amount of IR light reflected by the fundus is related to the illumination timing required for a quality image capture. These levels have been determined based on the results of images (and/or videos) collected during the development of the image capture timing determination engine 530. The lookup table (i.e., the image capture setting table) can be referenced based on the mean intensity of the IR light in the input image frame. In some embodiments, the illumination time returned is a combination of lead time and flash time. The lookup table can be created based on empirical data including captured images at different brightness levels. The image capture timing determination engine 530 is configured to interpret the lead and flash times from the illumination value returned.

At operation 576, the image capture timing determination engine 530 outputs the desired image capture setting (e.g., the illumination setting) as selected at the operation 574.

Figure 19:
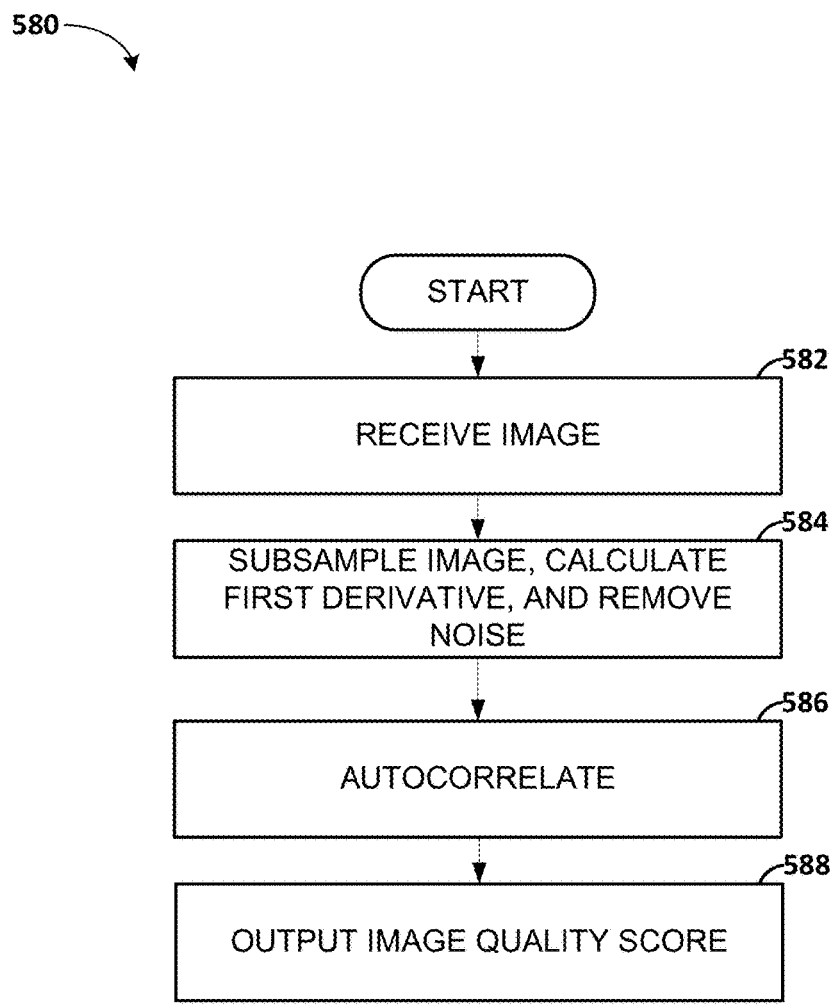
FIG. 19 is a flowchart illustrating an example method for operating an image quality detection engine of FIG. 17.

FIG. 19 is a flowchart illustrating an example method 580 for operating the image quality detection engine 532 of FIG. 17. In general, the image quality detection engine 532 includes an autocorrelation function that computes the focus quality of an image. A higher score can mean a better-focused image. Some examples of fundus camera operate to take several images at different focal distances, and the score resulting from the autocorrelation can be used to rank multiple similar images with different focal distances.

At operation 582, the image quality detection engine 532 can receive an image buffer. In some embodiments, the image is one-channel image. By way of example, only the Y-channel of a YUV image is passed to the image quality detection engine 532. The image can be of different dimension. In some embodiments, the images have 640×480 pixels.

At operation 584, the image quality detection engine 532 operates to subsample the image, calculate a first derivative, and remove noise. In some embodiments, to calculate the image quality score, a horizontal line of the image is isolated near the center of the picture. A sub sampling of the values is performed and the first derivative is obtained. Any values of the first derivative that are below a certain threshold are set to zero to remove noise.

At operation 586, the image quality detection engine 532 performs autocorrelation. In some embodiments, the sum of the product of the first derivative with itself produces the autocorrelation result. The intensity difference between neighboring pixels can be higher in the focused image when using the derivative approach. Any number of lines can be scored and added together for a total, but for performance reasons only a small number of lines currently used. The location of the lines generates a bias towards those locations, so the image quality score can select images that are better focused at the center of the image.

At operation 588, the image quality detection engine 532 outputs an image quality score generated based on the autocorrelation result.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

The description and illustration of one or more embodiments provided in this application are not intended to limit or restrict the scope of the present disclosure in any way. The embodiments, examples, and details provided in this application are considered sufficient to convey possession and enable others to make and use the best mode of claimed invention. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the present disclosure and the general inventive concept embodied in this application that do not depart from the broader scope.

What is claimed is:

1. A method of automatically capturing a fundus image of an eye, the method comprising:
   retrieving at least one first image from an image sensor device;
   processing, using at least one computing device, the at least one first image digitally to generate a processed image, including:
   downsampling the at least one first image;
   converting the at least one first image into at least one monochromatic image;
   applying a mask to remove a portion of the at least one first image;
   processing the at least one first image for scaling and calculating absolute values of array element associated with the at least one first image to generate a result, and converting the result to unsigned 8 bit;
   calculating a mean and standard deviation of the array elements associated with the at least one first image;
   calculating a slope of the mean; and
   determining the mean, standard deviation, and slope are within a predetermined range;
   detecting, using the at least one computing device, at least one point of interest in the processed image;
   determining, with the at least one computing device, whether the at least one point of interest is representative of a corresponding feature of the eye; and
   capturing the fundus image of the eye based on the at least one first image.

2. The method of claim 1, wherein applying the mask is calculated on an image that is scaled, cropped, and gray-scaled.

3. The method of claim 1, wherein:
retrieving at least one first image from an image sensor device comprises retrieving a plurality of first images, the plurality of first images captured by the image sensor device in sequence;
processing the at least one first image to generate a processed image comprises processing the plurality of first images to generate a plurality of processed images, respectively; and
detecting at least one point of interest in the processed image comprises detecting a point of interest in each of the plurality of processed images.

4. The method of claim 3, wherein the determining that each of the at least one point of interest is representative of a corresponding feature of the eye comprises:
comparing locations of the at least one point of interest in the processed image; and
determining that the locations are substantially the same in the processed image.

5. The method of claim 3, wherein the determining that each of the at least one point of interest is representative of a corresponding feature of the eye comprises:
comparing sizes of the at least one point of interest in the processed image; and
determining that the sizes are substantially the same in the processed image.

6. The method of claim 1, wherein obtaining the fundus image comprises:
determining if one of the at least one first image has a predetermined characteristic;
if one of the at least one first image has the predetermined characteristic, saving that image as the fundus image.

7. The method of claim 6, wherein the predetermined characteristic is associated with at least one of image quality and image size.

8. The method of claim 1, further comprising:
displaying the fundus image through a display device.

9. An image capture device comprising:
a processing device configured to control the image capture device; and
a computer readable data storage device storing software instructions that, when executed by the processing device, cause the image capture device to:
retrieve at least one first image from an image sensor device;
process the at least one first image digitally to generate a processed image, including:
reduce a size of the at least one first image;
convert the at least one first image into at least one monochromatic image;
apply a mask to remove a portion of the at least one first image;
process the at least one first image for scaling and calculating absolute values of array element associated with the at least one first image to generate a result, and converting the result to unsigned 8 bit;
calculate a mean and standard deviation of the array elements associated with the at least one first image;
calculate a slope of the mean; and
determine the mean, standard deviation, and slope are within a predetermined range;
detect at least one point of interest in the processed image;
determine whether the at least one point of interest is representative of a corresponding feature of an eye; and
capture a fundus image of the eye based on the at least one first image.

10. The image capture device of claim 9, wherein applying the mask is calculated on an image that is scaled, cropped, and grayscaled.

11. The image capture device of claim 9, wherein the software instructions cause the image capture device to:
retrieve a plurality of first images, the plurality of first images captured by the image sensor device in sequence;
process the plurality of first images to generate a plurality of processed images; and
detect a point of interest in each of the plurality of processed images.

12. The image capture device of claim 11, wherein the software instructions cause the image capture device to:
compare locations of the point of interest in the processed image; and
determine that the locations are substantially the same in the processed image.

13. The image capture device of claim 11, wherein the software instructions cause the image capture device to:
compare sizes of the at least one point of interest in the processed image; and
determine that the sizes are substantially the same in the processed image.

14. The image capture device of claim 9, wherein the software instructions cause the image capture device to:
determine if one of the at least one first image has a predetermined characteristic;
if one of the at least one first image has the predetermined characteristic, save that image as the fundus image; and
if none of the at least one first image has the predetermined characteristic, prompt the image sensor device to capture a second image and save the second image as the fundus image, the second image having the predetermined characteristic.

15. The image capture device of claim 14, wherein the predetermined characteristic is associated with at least one of image quality and image size.

16. A system of automatically capturing a fundus image of an object, the system comprising:
an image capture device configured to capture an image of the object;
an image process device programmed to:
retrieve a plurality of first images from the image capture device;
process the plurality of first images digitally to generate a plurality of processed images, including:
downsampling the at least one first image;
converting the at least one first image into at least one monochromatic image;
applying a mask to remove a portion of the at least one first image;
process the at least one first image for scaling and calculating absolute values of array element associated with the at least one first image to generate a result, and converting the result to unsigned 8 bit;
calculate a mean and standard deviation of the array elements associated with the at least one first image;
calculate a slope of the mean; and determine the mean, standard deviation, and slope are within a predetermined range;
detect points of interest in each of the plurality of processed images;
determine that locations and sizes of the points of interest are substantially the same among the plurality of processed images;
determine if one of the plurality of first images has a predetermined characteristic; and
if one of the plurality of first images has the predetermined characteristic, save that image as the fundus image; and
a display device configured to display the fundus image.

* * * * *